(12) United States Patent  (10) Patent No.: US 8,586,011 B2
Lowndes et al.  (45) Date of Patent: Nov. 19, 2013

(54) SKIN COATING COMPOSITION AND USES THEREOF

(75) Inventors: Linda Jane Lowndes, Queensland (AU); Leslie Pascoe, New South Wales (AU)

(73) Assignee: Blonde Holdings Pty Ltd. (AU)

( * ) Notice: Subject to any disclaimer, the term of this patent is extended or adjusted under 35 U.S.C. 154(b) by 432 days.

(21) Appl. No.: 12/830,674

(22) Filed: Jul. 6, 2010

(65) Prior Publication Data

US 2010/0297043 A1  Nov. 25, 2010

Related U.S. Application Data

(63) Continuation-in-part of application No. 11/658,941, filed as application No. PCT/AU2005/001120 on Jul. 29, 2005, now abandoned.

(30) Foreign Application Priority Data

Jul. 29, 2004  (AU) ................................ 2004904224
Jul. 29, 2004  (AU) ................................ 2004904225

(51) Int. Cl.
*A61K 36/00* (2006.01)
*A61K 8/96* (2006.01)
*A61K 35/64* (2006.01)
*A61K 8/98* (2006.01)
*A61Q 1/02* (2006.01)
*A61Q 17/04* (2006.01)
*A61P 17/00* (2006.01)

(52) U.S. Cl.
USPC ........... 424/59; 424/195.18; 424/64; 424/401

(58) Field of Classification Search
USPC ................................. 424/59, 195.18, 64, 401
See application file for complete search history.

(56) References Cited

U.S. PATENT DOCUMENTS

| | | |
|---|---|---|
| 2,230,063 A | 1/1941 | Klimist |
| 2,435,005 A | 1/1948 | Huppke |
| 4,379,136 A | 4/1983 | Mochida |
| 4,601,905 A | 7/1986 | Szeles |

(Continued)

FOREIGN PATENT DOCUMENTS

| | | |
|---|---|---|
| EP | 0 158 412 | 10/1985 |
| EP | 0158412 | 10/1985 |

(Continued)

OTHER PUBLICATIONS

International Search Report; PCT/AU2005/001120; Sep. 21, 2005.

(Continued)

*Primary Examiner* — Ernst Arnold
*Assistant Examiner* — Hong Yu
(74) *Attorney, Agent, or Firm* — Cantor Colburn LLP

(57) ABSTRACT

A composition for coating skin comprising shellac, ethanol, castor oil, ethyl cellulose and fumed silica or nano zinc oxide, wherein the composition forms a long lasting waterproof flexible film on skin. The composition may include different ingredients for different applications. In one embodiment, the composition includes pigment and/or dye and may be used to coat a skin blemish such that the skin blemish blends in with the surrounding skin. In another embodiment, the composition includes a sunscreen agent and may be used as a sunscreen. In yet another embodiment, the composition includes a therapeutic agent for treating a disorder of the skin.

38 Claims, 5 Drawing Sheets

(56) References Cited

U.S. PATENT DOCUMENTS

| | | | |
|---|---|---|---|
| 4,810,490 | A | 3/1989 | Dixon et al. |
| 4,853,222 | A | 8/1989 | Avalle |
| 5,980,921 | A * | 11/1999 | Biedermann et al. .......... 424/401 |
| 6,284,233 | B1 * | 9/2001 | Simon et al. ................ 424/78.03 |
| 6,726,916 | B1 * | 4/2004 | Ramin ........................... 424/401 |
| 6,905,696 | B2 | 6/2005 | Marotta et al. |
| 7,323,162 | B2 | 1/2008 | Martin et al. |
| 2002/0128615 | A1 * | 9/2002 | Tyrrell et al. .................. 604/364 |
| 2002/0197221 | A1 | 12/2002 | Nichols et al. |
| 2003/0152540 | A1 * | 8/2003 | Putman et al. ............... 424/70.1 |
| 2004/0086473 | A1 | 5/2004 | Rabe et al. |
| 2005/0171052 | A1 | 8/2005 | Cook et al. |
| 2005/0232876 | A1 | 10/2005 | Minga et al. |
| 2006/0110347 | A1 | 5/2006 | Lu et al. |
| 2007/0104850 | A1 | 5/2007 | Cook et al. |
| 2007/0196295 | A1 | 8/2007 | Cantwell et al. |
| 2008/0081022 | A1 | 4/2008 | Yu et al. |
| 2008/0305062 | A1 | 12/2008 | Bui et al. |
| 2009/0035365 | A1 | 2/2009 | Popplewell et al. |

FOREIGN PATENT DOCUMENTS

| | | |
|---|---|---|
| FR | 2932985 | 1/2010 |
| GB | 525337 | 8/1940 |
| GB | 1180968 | 2/1970 |
| JP | 2003261422 | 9/2003 |
| WO | WO 98/35709 | 8/1998 |
| WO | WO9850002 | 11/1998 |
| WO | WO 02/094205 | 11/2002 |
| WO | WO2009156375 | 12/2009 |

OTHER PUBLICATIONS

Pharmaceutical Formulas P.F. vol. 1 "The Chemist & Druggist" Book of Formulas, Twelfth Edition revised and extended, Published at the Offices of The Chemist and Druggist, London, 1953, pp. 71-79, pp. 565-571 and pp. 897-899.

The Pharmaceutical Recipe Book, Second Edition, (R.B.II), by Authority of the American Pharmaceutical Association, Published by The American Pharmaceutical Association (1936), pp. 12-14.

Cosmetic and Toiletry Formulations, by Flick, E. W., Noyes Publications, New Jersey, USA (1984), p. 138 Skin Paint—Waterproof (CMC/Pigment/Wax).

Smith & Nephew, products, transparent Film Dressings, OpSite* Spray (online), (retrieved on Sep. 5, 2005). Retrieved from the Internet <URL: http://wound.smith-nephew.com/za/Product.asp?NodeID=536>first published on the www on Sep. 24, 2003.

Johnson & Johnson Band-Aid Brand Liquid Bandage (online), (retrieved on Sep. 5, 2005). Retrieved from Internet <URL: http://web.archive.org/web/20021215080619/http://www.jnj.com/innovations/new_features/BANDAID_Brand_Liquid_Bandage.htm>first published on the www on Dec. 15, 2002.

Elastoplast Spray Bandage (online), (retrieved on Sep. 5, 2005). Retrieved from the Internet, URL: http:/web.archive.org/web/*/http://www.elastoplast.com.au/products_spray.asp>first published on the www on Jun. 10, 2004.

Allen, L.V., "Compounding lacquers, varnishes, collodions and protectants," Secundum Artem Current & Practical Compounding Information for the Pharmacist vol. 13 No. 3 (online), (retrieved on Sep. 5, 2005). Retrieved from the Internet <URL: http://www/paddocklabs.com/secundum_artem.html>.

IGIA 2 Instant Cover 3-shade Concealer set (online), (retrieved on Sep. 15, 2005). Retrieved from the Internet <URL: http://web.archive.org/web/20030715184456/http://secure.igia.co/prodetail.cfm?ID=AT7623>first published on the www on Jul. 15, 2003.

Derwent Abstract Accession No. 87-278419/40, Class D21, DD 245815 A (Veb Kosmetik Komb) May 30, 1987.

Examiners Report, AU 2005266857, Apr. 1, 2010.

ER AU 2010202841 dtd Feb. 20, 2012.

Office Action, India, 646KOLNP2007, Oct. 11, 2010.

\* cited by examiner

SKIN COATING COMPOSITION AND USES THEREOF

CROSS REFERENCE TO RELATED APPLICATIONS

This application is a continuation-in-part of and claims the benefit of U.S. patent application Ser. No. 11/658,941 filed on 29 Jan. 2007, which is the U.S. national phase entry of International Patent Application No. PCT/AU2005/001120 filed on 29 Jul. 2005, which claims priority to Australian Patent Application No. 2004904225 filed on 29 Jul. 2004, and Australian Patent Application No. 2004904224 filed on 29 Jul. 2004, all of which said applications are incorporated herein by reference in their entirety.

FIELD OF THE INVENTION

The present invention generally relates to a composition for coating skin wherein the composition forms a durable waterproof flexible film on skin. The composition may include different ingredients for different applications. In one embodiment, the composition includes pigment and/or dye and may be used to coat a skin blemish such that the skin blemish blends in with the surrounding skin. In another embodiment, the composition includes a sunscreen agent and may be used as a sunscreen. In yet another embodiment, the composition includes a therapeutic agent for treating the skin.

The subject matter of this application is related to the applicant's International Patent Application, No. PCT/AU2005/00119, filed on 29 Jul. 2005 and entitled "A Colour Compensating System" as well as Australian Provisional Patent Application No. 2004904225, the entire contents of which are herein incorporated by cross-reference.

BACKGROUND OF THE INVENTION

Compositions for coating skin are known. Some are in the form of cosmetics for masking skin discoloration and skin blemishes, others are in the form of sunscreens for providing protection against the adverse effects of solar radiation, and yet others are in the form of skin care products for promoting healthy skin.

Some of the known skin coating compositions have the disadvantage that they are not long-lasting on the skin and may require frequent reapplication. Some compositions may be readily rubbed off the skin, whereas other compositions may be readily washed off the skin by way of sweat or when in contact with water.

SUMMARY OF THE INVENTION

The present invention broadly relates to a coating composition that, when applied to the skin, forms a durable waterproof (i.e. impervious to water) flexible film.

According to a first aspect of the present invention, there is provided a coating composition for skin, said composition comprising resin and flexibilizer, wherein upon application to skin, said composition forms a waterproof flexible film.

According to a second aspect of the invention, there is provided a method for coating skin comprising the steps of:
(i) coating skin with a composition comprising resin and flexibilizer; and
(ii) allowing the composition to form a waterproof flexible film over the skin.

Preferably, the flexible film is durable and is capable of remaining adhered to the skin for 1 to 3 days and more preferably up to about 5 days. The durability of the film will depend, inter alia, on the composition of the film, the properties of the skin and the environmental conditions to which the skin and film are subjected.

The properties of the film will depend on the choice and quantity of resin and flexibilizer. The properties of the film may be adjusted as necessary by changing the ingredients of the composition as well as by varying the relative amounts of ingredients. Other ingredients (eg. diluent/viscosity modifier, thickener and adhesive) may be added to the composition, and these will also affect the properties of the film.

The composition may be, for example, in the form of, or applied as, a paste, cream, gel, viscous solution, solution, suspension, dispersion, liquid, spray or aerosol. The film may be opaque, translucent or transparent.

The composition may be used as a bandage, artificial skin or otherwise as a barrier to protect the skin beneath from the environment.

In one embodiment, the composition may protect the skin beneath from fluids, such as liquids or gases, or particulate matter, such as dirt. The skin may be protected by fluids or other matter discharged from the wearer's body, such as urine, faecal matter or vomit, which could damage or sensitise the skin or otherwise cause pain to the wearer. For example, the composition may be applied to skin in a vicinity of the wearer's anus such that the skin is protected from acidic matter discharged from the anus.

In another embodiment, the composition may be used as a barrier or bandage, for trapping or otherwise keeping one or more therapeutic agents between the composition and the skin. It is possible that the composition may actually bond with the therapeutic agent that has been applied to the skin. It is possible that the composition may form a physical layer over the therapeutic agent and skin beneath.

Any suitable type and quantity of therapeutic agent may be used. A therapeutic agent as described herein is an agent that has medicinal or cosmeceutical properties or other properties of advantage to the wearer. A suitable therapeutic agent may be an antimicrobial such as a bactericide or fungicide or an antiseptic agent. Another suitable therapeutic agent may promote wound healing or have anti-inflammatory properties. Yet another suitable therapeutic agent may be a steroid or hormone for treating eczema or dermatitis, for example. Yet other suitable therapeutic agents may be, for example, anti-acne agents, analgesics, anesthetic agents, anticancer agents, anti-causative agents, antihistamines, anti-scarring agents, anti-ulcer agents, antivirals, burn-healing agents, cell stimulants and proliferants, chemotherapeutic agents, emolients, hair-growth promoting agents, depigmenting agents, insect-bite treating agents, insecticides or insect repellants, minerals, proteins, peptides and DNA molecules. Such therapeutic agents are well known in the art and are described in the Merck Index, $14^{th}$ edition. Examples of suitable therapeutic agents include vitamins, such as vitamin E, rosehip oil and kikui oil. Examples of suitable growth factors are described, for example, in the specification published as WO92/09301 to the American National Red Cross.

The composition may include a diluent (which is a viscosity modifier). Any suitable type of diluent may be used. The composition may include more than one type of diluent/viscosity modifier. Any suitable quantity of diluent may be used. For instance, the composition may contain little diluent if applied to the skin as a paste, viscous solution or spreadable gel-like material, e.g. using a brush or sponge. The composition may contain more diluent if applied to the skin as a liquid or solution, e.g. using an airbrushing or spray gun. The composition may be in the form of an aerosol, packaged under pressure with a suitable gaseous propellant. The diluent may be evaporative.

The diluent may be a primary alcohol (C2-C4), such as ethanol, propanol, isopropanol, n-butanol or isobutanol, for example. Preferably, the diluent is an alcohol, such as ethanol, which will readily evaporate. The alcohol may be denatured or non-denatured. Ethanol or other primary alcohol (either denatured with IPA or not) may be present in the composition in any suitable amount but is preferably present in an amount of about 20-80% weight by weight (w/w), more preferably about 40-90% w/w, and even more preferably about 50-80% w/w. Depending on how the composition is applied, it is possible that the amount of alcohol could fall out side of the specified ranges. For example, if applied as a spray, the amount of ethanol may exceed 90% w/w as, upon evaporation, the film would still form.

Any suitable type of resin may be used. The resin may act both as a film-former (binder) and waterproofing agent. The composition may include more than one type of resin. The resin may be of natural or synthetic origin. Any suitable quantity of resin may be used. The resin may be an alcohol-soluble resin or a substantially alcohol-soluble resin. The resin may be, for example, a natural gum derivative or polysaccharide. Natural gum derivatives include, for example, solidified plant saps, such as asafetida, gutta-percha, gamboges, gum Arabic, balata gum, gum tragacanth and karaya gum. The resin may be a shellac. The resin may be shellac, rosin, copal, dammar or balsam. Preferably, the resin is de-waxed (blonde) bleached shellac.

Shellac or at least one other type of resin/natural gum may be present in the composition in any suitable amount but is preferably present in an amount of about 1-40% w/w, more preferably about 1-30% w/w, and even more preferably about 4-30% w/w.

Any suitable type of flexibilizer (plasticiser) may be used to impart flexibility to the film and to hinder flaking of the film from the skin. The flexibilizer may help in forming the film. The composition may include more than one type of flexibilizer. Any suitable quantity of flexibilizer may be used. A suitable flexibilizer may be oil, such as a non-drying or semi-drying oil. The oil may be of animal, vegetable, mineral or synthetic origin. Examples of suitable non-drying or semi-drying oils include pine oil, eucalyptus oil, ti-tree oil, rosehip oil, soya bean oil, coconut oil, castor oil, olive oil, safflower oil and sunflower oil or a mixture thereof. The oil is preferably castor oil.

Oil, such as castor oil or a mixture of oils, may be present in the composition in any suitable amount but is preferably present in an amount of about 2-80% w/w, more preferably about 3-70% w/w, and even more preferably about 7-30% w/w.

The composition may include a cellulosic preparation. A cellulosic preparation is an example of another suitable flexibilizer. Any suitable type of cellulosic preparation may be used. The cellulosic preparation may comprise, for example, ethyl cellulose, cellulose acetate, sucrose acetate isobutyrate, nitrocellulose and cellulose acetate propionate.

A cellulosic preparation, such as ethyl cellulose or a mixture of different cellulosic preparations, may be present in the composition in any suitable amount but is preferably present in an amount of about 0.1-20% w/w, more preferably about 0.5-15% w/w, and even more preferably about 0.5-10% w/w.

The composition may include an adhesive for improving attachment of the film to the skin. Any suitable type of adhesive may be used. The composition may include more than one type of adhesive. Any suitable quantity of adhesive may be used. Preferably, the adhesive is a cellulosic preparation such as, for example, ethyl cellulose or sucrose acetate isobutyrate.

An adhesive, such as ethyl cellulose or a mixture of different cellulosic preparations, may be present in the composition in any suitable amount but is preferably present in an amount of about 0.1-20% w/w, more preferably about 0.5-15% w/w, and even more preferably about 0.5-10% w/w.

The composition may include an anti-agglomeration agent or dispersing agent that alters the wetting action to surface energy effects. Any suitable agent or agents and quantity/quantities thereof may be used. A suitable agent may be, for example, a blend of neutralised acid esters of phosphoric acid together with 2-(2-butoxyethoxy)ethanol. Other examples include lecithins such as soya lecithin, and ethoxylated oils such as ethoxylated castor oil.

The composition may include thickener to increase the viscosity of the composition. The thickener may act as a suspending agent. Any suitable type of thickener may be used. The composition may include more than one type of thickener. Any suitable quantity of thickener may be used. A suitable thickener may include, for example, one or more of the following: a cellulosic preparation (as described above) or an inorganic thickener such as silicon dioxide (fumed silica), castor oil derivatives, quaternium ammonium compound of bentonite, smectite, laponite, hectorite, zinc stearate, zinc oxide (an example of zinc oxide is sold under the trade mark Zinclear™) including nano zinc oxide, inorganic thixotrope or modified clays. A preferred inorganic thickener is fumed silica (Aerosil COK84).

A thickener, such as an inorganic thickener, or a mixture of different thickeners, may be present in the composition in any suitable amount but is preferably present in an amount of about 0.1-20% w/w, more preferably about 0.1-10% w/w, and even more preferably about 0.5-10% w/w.

The composition may include a preservative/stabilizer for extending the shelf life of the composition. Any suitable type of preservative/stabilizer may be used. The composition may include more than one type of preservative/stabilizer. Any suitable quantity of preservative/stabilizer may be used. A suitable preservative/stabilizer may include, for example, one or more of the following: butylated hydroxytoluene (BHT), butylated hydroxyanisole, hydroquinone and methylhydroquinone.

A preservative/stabilizer or a mixture of different preservatives/stabilizers, may be present in the composition in any suitable amount but is preferably present in an amount of about 0.1-10% w/w, more preferably about 0.5-5% w/w, and even more preferably about 0.5-10% w/w.

The film is preferably highly resistant to being washed off with water. The film may remain intact even when immersed in hot water. The film preferably bonds to the skin when immersed in saltwater. The film is preferably highly resistant to being rubbed off. The film may remain attached to the skin even if a shaver is scraped over the film. If more than one film layer is applied to the skin, the film layers may bond to one another. Preferably, the film enables the skin to breathe. It appears that the skin is able to breathe in that the film does not completely seal sweat pores of the skin as well as perhaps hair follicles of the skin.

According to one preferred form of the invention, the coating composition comprises:
 about 5-30% w/w natural gum derivative;
 about 50-80% w/w alcohol;
 about 2-70% w/w oil;
 about 2-10% w/w cellulosic preparation; and
 about 0.5-10% w/w inorganic thickener.

Preferably, the natural resin/gum derivative is shellac, the alcohol is denatured ethanol, the oil is castor oil (7-65% w/w) or a mixture of castor oil (7-65% w/w) and rosehip oil (0.1-5% w/w), the cellulosic preparation is ethyl cellulose, and the inorganic thickener is silicon dioxide.

Preferably, the preferred form further comprises about 0.5-3% w/w preservative, such as BHT.

According to another preferred form of the invention, the coating composition comprises:
- about 1-30% w/w substantially alcohol soluble resin/natural gum derivative as a film-former and waterproofing agent;
- about 40-90% w/w primary alcohol as a diluent and viscosity modifier;
- about 2-70% w/w non-drying or semi-drying oil as a film-former and flexibilizer;
- about 0.5-10% w/w cellulosic preparation as a flexibilizer and/or adhesive; and
- about 0.1-10% w/w inorganic thickener.

According to yet another preferred form of the invention, the coating composition comprises:
- about 1-30% w/w substantially alcohol soluble resin/natural gum derivative such as shellac;
- about 40-90% w/w primary alcohol such as ethanol;
- about 2-70% w/w non-drying or semi-drying oil such as castor oil;
- about 0.5-10% w/w cellulosic preparation such as ethyl cellulose; and
- about 0.1-10% w/w inorganic thickener such as fumed silica.

According to yet another particularly preferred form of the invention, for application to the skin as a liquid, the coating composition comprises:
- about 4% w/w substantially alcohol soluble resin/natural gum derivative such as shellac;
- about 62% w/w primary alcohol such as ethanol;
- about 26% w/w non-drying or semi-drying oil such as castor oil;
- about 6% w/w cellulosic preparation such as ethyl cellulose; and
- about 2% w/w inorganic thickener such as fumed silica.

According to yet another particularly preferred form of the invention, the coating composition, in a diluted form suitable for application as a spray, comprises:
- about 1.2% w/w substantially alcohol soluble resin/natural gum derivative such as shellac;
- about 88.2% w/w primary alcohol such as ethanol;
- about 8% w/w non-drying or semi-drying oil such as castor oil;
- about 2% w/w cellulosic preparation such as ethyl cellulose; and
- about 0.6% w/w inorganic thickener such as fumed silica.

The coating composition according to the first aspect of the invention may include different ingredients for different applications. For example, the coating composition may include at least one pigment and/or dye and be used to coat discoloured skin or a skin blemish such that the discoloured skin or skin blemish blends with the surrounding skin. The skin discoloration/skin blemish may be due to, for example, a birthmark, a mole, a basal cell carcinoma, vitiligo, a scar, a burn, pigmentation, acne, a vein, tattoo, eczema, dermatitis or bruising. Alternatively, such a composition may be used to simply change the skin colour of an individual.

Alternatively or additionally, the coating composition may include at least one sunscreen agent and be used as a sunscreen. The sunscreen may protect individuals against premature ageing of skin, skin cancer and other harmful effects of solar radiation.

Alternatively or additionally, the coating composition may include at least one therapeutic agent for preventing or treating disorders of the skin—for example, cuts, inflammation or infections.

According to a third aspect of the present invention, there is provided a coloured coating composition for skin, said composition comprising resin, flexibilizer and pigment and/or dye, wherein upon application to skin, said composition forms a waterproof flexible coloured film.

According to one preferred form of the invention, the coloured coating composition comprises:
- about 5-30% w/w natural gum derivative;
- about 50-80% w/w alcohol;
- about 2-70% w/w oil;
- about 2-10% w/w cellulosic preparation;
- about 0.5-10% w/w inorganic thickener; and
- at least one pigment and/or dye.

According to another preferred form of the invention, the coloured coating composition comprises:
- about 1-30% w/w substantially alcohol soluble resin/natural gum derivative as a film-former and waterproofing agent;
- about 40-90% w/w primary alcohol as a diluent and viscosity modifier;
- about 2-70% w/w non-drying or semi-drying oil as a film-former and flexibilizer;
- about 0.5-10% w/w cellulosic preparation as a flexibilizer and/or adhesive;
- about 0.1-10% w/w inorganic thickener; and
- at least one pigment and/or dye.

According to yet another preferred form of the invention, the coloured coating composition comprises:
- about 1-30% w/w substantially alcohol soluble resin/natural gum derivative such as shellac;
- about 40-90% w/w primary alcohol such as ethanol;
- about 2-70% w/w non-drying or semi-drying oil such as castor oil;
- about 0.5-10% w/w cellulosic preparation such as ethyl cellulose;
- about 0.1-10% w/w inorganic thickener such as fumed silica; and
- at least one pigment and/or dye.

According to yet another particularly preferred form of the invention, for application to the skin as a liquid, the coloured coating composition comprises:
- about 4% w/w substantially alcohol soluble resin/natural gum derivative such as shellac;
- about 53% w/w primary alcohol such as ethanol;
- about 26% w/w non-drying or semi-drying oil such as castor oil;
- about 6% w/w cellulosic preparation such as ethyl cellulose;
- about 2% w/w inorganic thickener such as fumed silica; and
- up to about 9% pigment and/or dye.

According to yet another particularly preferred form of the invention, the coloured coating composition, in a diluted form suitable for application as a spray, comprises:
- about 1.2% w/w substantially alcohol soluble resin/natural gum derivative such as shellac;
- about 86% w/w primary alcohol such as ethanol;
- about 8% w/w non-drying or semi-drying oil such as castor oil;
- about 2% w/w cellulosic preparation such as ethyl cellulose;
- about 0.6% w/w inorganic thickener such as fumed silica; and
- up to about 2.2% pigment and/or dye.

Any suitable type of pigment or dye may be used. The composition may include more than one type of pigment and/or dye, depending on the desired colour for the film. Any suitable quantity of pigment or dye may be used. Preferably, the pigment and/or dye is present in amount of about 0.01-15% w/w and more preferably about 0.01-10% w/w. A suitable pigment or dye may include, for example, one or more of the following:

Natural or synthetic iron oxides, black, red, yellow, brown, blended in various ratios.
Rutile titanium dioxide (micronised).
Zinc oxide (micronised).
Ultramarine blue (micronised).
Mixed metal oxide (cobalt) blue, black, turquoise, green.
Bon arymadide red pigments.
Bon red (calcium).
Rubine toners.
Arylamide yellows.
Transparent iron oxide pigments.
Phthalocyanine blues.
Dioxazine violets.
Pearlescent pigments in various colours, including white, copper, bronze.
Solvent dyes red, orange, yellow, blue, violet, brown, black.

Preferably, the pigment is micronised and uniformly dispersed throughout the film.

According to a fourth aspect of the present invention, there is provided a method for coating a skin discoloration or skin blemish such that the skin discoloration or blemish blends with the surrounding skin, said method comprising the steps of:

(i) coating a skin discoloration or blemish with a composition comprising resin, flexibilizer, and pigment and/or dye; and (ii) allowing the composition to form a waterproof flexible coloured film over the skin discoloration or blemish.

The method may further comprise the step of (iii) applying a fixing powder to the coated skin discoloration or blemish to create a matte effect and to produce a more natural skin appearance. The fixing powder may be applied immediately after application of the composition and then reapplied after washing the skin. The application of a fixing powder is preferred if the composition is applied to the skin as a spray.

The fixing powder may be of any suitable composition. The fixing powder can comprise talc, kaolin, zinc stearate, silicone oil (dimethicone), propylene glycol, and one or more preservatives such as, for instance, methylparaben, propylparaben, ethylparaben, butylparaben and mydazolidinyl urea. Talc and kaolin are opaquing agents. Zinc stearate is a lubricant. Dimethicone aids in spreading and rubbing of the powder on the skin and acts as a barrier preventing water penetration. Propylene glycol is a solvent. The fixing powder may also reduce any stickiness of an exposed surface of the film.

In a preferred form the fixing powder comprises:
about 93% w/w talc;
about 4.7% w/w zinc stearate;
about 1.4% w/w silicone oil; and
about 0.9% w/w Unigerm G2™ (mixture of methylparaben, ethylparaben, propylene glycol and mydazolidinyl urea).

The method preferably comprises the step of cleaning the skin (of natural oils, cosmetics etc.) before applying the coating composition.

The method may comprise additional initial steps of:
measuring at least one colour property of the skin discoloration or blemish;
measuring at least one colour property of the surrounding skin; and
using the measured at least one colour property of the skin discoloration or blemish and the at least one colour property of the surrounding skin to formulate a composition having a compensatory colour such that the skin discoloration or blemish when coated with the composition blends with the surrounding skin.

Details of these additional initial steps may be found in the applicant's co-pending International Patent Application entitled "A Colour Compensating System" as well as in Provisional Patent Application No. 2004904225.

The coloured coating composition preferably has a degree of translucency when applied to the skin discoloration or blemish and is not of identical colour to the surrounding skin. The present inventor has found that previous attempts to cover discoloured skin/blemishes by selecting an opaque cosmetic coating that is exactly the same colour as the surrounding skin and subsequently applying that coating to the skin discoloration/blemish to hide or mask the discoloration/blemish resulted in an unnatural and overly-made up, almost plasticky, look. Rather than simply trying to hide the discoloration/blemish, the translucent coating can have an additive or complementary effect with the underlying discoloration/blemish such that the discoloration/blemish, when coated, has a more natural appearance whilst still matching the appearance of the surrounding skin.

According to a fifth aspect of the present invention, there is provided a sunscreen composition for skin, said composition comprising resin, flexibilizer and an effective amount of sunscreen agent, wherein upon application to skin, said composition forms a waterproof flexible film capable of providing the skin with sun protection.

Any suitable type of sunscreen agent may be used. The composition may include one or more sunscreen agents. Any suitable quantity of sunscreen agent or agent mixture may be used. Suitable sunscreen agents include organic chemical compounds that absorb ultraviolet light, inorganic particulates that reflect, scatter, and absorb UV light, and organic particulates that mostly absorb light.

Possible sunscreen agents include p-aminobenzoic acid, octyldimethyl-PABA, phenylbenzimidazole sulfonic acid, 2-ethoxyethyl p-methoxycinnamate, dioxybenzone, oxybenzone, benzophenone-8, benzophenone-3, homomethyl salicylate, menthyl anthranilate, octocrylene, 2-cyano-3,3diphenyl acrylic acid, octyl methoxycinnamate, 2-ethylhexylester, cinoxate, homosalate, octyl salicylate, sulisobenzone, trolamine salicylate, avobenzone, ecamsule, titanium dioxide, zinc oxide, bisoctrizole, methylene bis-benzotriazolyl tetramethylbutylphenol, bis-ethylhexyloxyphenol methoxyphenol triazine, bemotrizinol, anisotriazine, bisdisulizole disodium, disodium phenyl dibenzimidazole tetrasulfonate, bisimidazylate, drometrizole trisiloxane, benzophenone-9, octyl triazone, ethylhexyl triazone, diethylamino hydroxybenzoyl hexyl benzoate, iscotrizinol, diethylhexyl butamido triazone, dimethico-diethylbenzalmalonate, 4-methylbenzylidene camphor, and isopentenyl-4-methoxycinnamate.

Preferred sunscreen agents include titanium dioxide and zinc oxide. Preferably, the composition includes zinc oxide. Zinc oxide below 100 nm is usually referred to as a nano particle sized product which is optically clear. Above 100 nm particle size the product generally becomes semi-translucent white and above 1000 nm the product generally becomes quite opaque white. If a clear sunscreen is desired, the zinc oxide may have a particle size of about 5-220 nm, 160-200 nm, 180-220 nm or 5-100 nm, and more preferably a particle size of about 20-40 nm. If a white opaque sunscreen is desired, the zinc oxide may have a larger particle size of about 400-1000 nm, for example.

The composition may have any defined SPF value or other value as defined by The Persistent Pigment Darkening (PPD) Method, Star Rating System, Immediate Pigment Darkening (IPD) Method, UV-A Standard Method, Protection Grade of UVA Method, UVA/UVB-ratio Method or Critical Wavelength Standard, for example.

Preferably, the SPF value is at least 15 and more preferably at least 30. The composition may be applied to the skin in layers so as to exceed an SPF value of 30. A multilayer film may provide an SPF value of over 1000.

Preferably, the sunscreen film is durable in that it need not be reapplied for at least 1 to 3 days and up to about five days.

The sunscreen composition may further include a pigment and/or dye for coating discoloured skin or skin blemishes, or for producing an opaque film. Individuals suffering from xeroderma pigmentosum may benefit from a long-lasting opaque sunscreen having a high SPF value. Such individuals may benefit from a multilayer film, whether the films are of the same composition or of different compositions. The sunscreen composition may further include a pigment and/or dye for providing the wearer with a bronzed appearance. Any suitable type of pigment and/or dye and quantity thereof may be used.

The sunscreen composition may further include an anti-causative agent or agents to absorb and mop-up free radicals, thus reducing the potential for a long-term skin deteriorating effect known as photoaging. Any suitable type of anti-causative agent and quantity thereof may be used. Examples include BASF's Uvinul A Plus (diethylamino hydroxybenzoyl hexyl benzoate) and Uvinul T 150 (ethylhexyl triazone). 3% w/w Uvinul A Plus and 1% w/w Uvinul T 150, for example, are believed to provide the skin with almost 100% antioxidant protection.

According to a preferred form of the invention, the sunscreen composition comprises:
about 5-30% w/w natural gum derivative;
about 20-60% w/w alcohol;
about 10-60% w/w sunscreen agent;
about 2-20% w/w oil; and
about 2-15% w/w cellulosic preparation.

Preferably, the natural gum derivative is shellac, the alcohol is denatured ethanol, the oil is castor oil (2-20% w/w) or a mixture of castor oil (2-15% w/w) and rosehip oil (0.1-5% w/w), the cellulosic preparation is ethyl cellulose, and the sunscreen agent is zinc oxide having a particle size of between about 5-100 nm or about 160-250 nm.

Preferably, the preferred form further comprises about 0.5-1% w/w preservative, such as BHT.

Preferably, the preferred form further comprises about 0.5-5% w/w vitamin E acetate.

According to another preferred form of the invention, the sunscreen composition comprises:
about 1-30% w/w substantially alcohol soluble resin/natural gum derivative as a film-former and waterproofing agent;
about 40-90% w/w primary alcohol as a diluent and viscosity modifier;
about 2-70% w/w non-drying or semi-drying oil as a film-former and flexibilizer;
about 0.5-10% w/w cellulosic preparation as a flexibilizer and/or adhesive;
about 0.1-10% w/w inorganic thickener; and
an effective amount of sunscreen agent.

According to yet another preferred form of the invention, the sunscreen composition comprises:
about 1-30% w/w substantially alcohol soluble resin/natural gum derivative such as shellac;
about 40-90% w/w primary alcohol such as ethanol;
about 2-70% w/w non-drying or semi-drying oil such as castor oil;
about 0.5-10% w/w cellulosic preparation such as ethyl cellulose; and
about 0.1-10% w/w inorganic thickener such as fumed silica; and
up to about 6.4% w/w sunscreen agent.

According to yet another particularly preferred form of the invention, for application to the skin as a liquid, the sunscreen composition comprises:
about 4% w/w substantially alcohol soluble resin/natural gum derivative such as shellac;
about 53% w/w primary alcohol such as ethanol;
about 26% w/w non-drying or semi-drying oil such as castor oil;
about 6% w/w cellulosic preparation such as ethyl cellulose;
about 2% w/w inorganic thickener such as fumed silica; and
up to about 9% w/w sunscreen agent.

According to yet another particularly preferred form of the invention, the sunscreen composition, in a diluted form suitable for application as a spray, comprises:
about 1.2% w/w substantially alcohol soluble resin/natural gum derivative such as shellac;
about 86% w/w primary alcohol such as ethanol;
about 8% w/w non-drying or semi-drying oil such as castor oil;
about 2% w/w cellulosic preparation such as ethyl cellulose;
about 0.6% w/w inorganic thickener such as fumed silica; and
up to about 2.2% w/w sunscreen agent.

According to a sixth aspect of the present invention, there is provided a therapeutic composition for skin, said composition comprising resin, flexibilizer and at least one therapeutic agent, wherein upon application to skin, said composition forms a waterproof therapeutic flexible film.

According to a seventh aspect of the present invention, there is provided a method for prevent or treating a disorder of the skin, said method comprising the step of applying to the skin a composition comprising resin, flexibilizer and at least one therapeutic agent, wherein upon application to skin, said composition forms a waterproof therapeutic flexible film.

According to an eighth aspect of the present invention, there is provided the use of a composition in the preparation of a medicament for the prevention or treatment of a skin disorder, said composition comprising resin, flexibilizer and at least one therapeutic agent, wherein said composition forms a waterproof therapeutic flexible film when applied to skin.

Any suitable type and quantity of therapeutic agent may be used. The composition may include one or more therapeutic agents. A therapeutic agent as described herein is an agent that has medicinal or cosmeceutical properties or other properties of advantage to the wearer. A suitable therapeutic agent may be an antimicrobial such as a bactericide or fungicide or an antiseptic agent. Another suitable therapeutic agent may promote wound healing or have anti-inflammatory properties. Yet other suitable therapeutic agents may be, for example, anti-acne agents, analgesics, anesthetic agents, anti-cancer agents, anti-causative agents, antihistamines, anti-scarring agents, anti-ulcer agents, antivirals, burn-healing agents, cell stimulants and proliferants, chemotherapeutic agents, emolients, hair-growth promoting agents, depigmenting agents, insect-bite treating agents, insecticides or insect repellants, minerals, proteins, peptides and DNA molecules. Such therapeutic agents are well known in the art and are described in the Merck Index, 14$^{th}$ edition. Examples of suitable therapeutic agents include vitamins, such as vitamin E, rosehip oil and kikui oil. Examples of suitable growth factors are described, for example, in the specification published as WO92/09301 to the American National Red Cross.

The therapeutic composition may include a pigment and/or dye for coating discoloured skin or skin blemishes and/or a sunscreen agent.

The disorder of the skin may be xeroderma pigmentosum.

As mentioned above, the therapeutic composition may further be used as a barrier or bandage, for trapping or otherwise keeping one or more therapeutic agents between the composition and the skin. It is possible that the composition may actually bond with the therapeutic agent that has been applied to the skin. It is possible that the composition may form a physical layer over the therapeutic agent and skin beneath.

According to a ninth aspect of the present invention, there is provided a method of coating skin of an individual having a sun-sensitive skin condition against harmful UV radiation, said method comprising the steps of:

(1) applying to the skin of the individual a fluorophore;

(2) applying to the skin of the individual at least one layer of a film-forming coating composition to completely cover the fluorophore, wherein the coating composition comprises resin, flexibilizer and an effective amount of at least one sunscreen agent, wherein upon application to skin, said composition forms a waterproof flexible film capable of providing the skin with protection against UV radiation; and (3) checking for fluorescence of the fluorophore using a UV light source, wherein fluorescence of the fluorophore indicates that further application of the composition to the skin is required.

Any suitable type and quantity of fluorophore can be used. For instance, 0.1-10% w/w could be used. Suitable fluorophores include long-wavelength fluorophores (LWFs) such as cyanines, oxazines, rhodamines and ruthenium(II) complexes. The fluorophore can be suspended in a carrier and suitable carriers include a coating composition described above, particularly a coloured film forming composition as described above. Preferably, the carrier enables the fluorophore to be spray applied to the skin. A preferred fluorophore is supplied by the Dayglow Colour Corp. under the number DGS-00 and can be used in a quantity of, say, 0.1-10% w/w (more preferably 3-5% w/w) fluorophore to, say, 90-99.9% w/w coloured film forming composition as described above. It may also be supplied by Interchem Pty Ltd as Pigment 2210 (with a zinc sulphide content greater than 75%). Another suitable fluorophore is the Neoface Blue™ fluorocolor Fluran as supplied by All Colour Supplies Pty Ltd.

As mentioned, the coating composition can be a coloured coating composition having UV-blocking pigments/dyes and/or a sunscreen composition as described above. One or more layers of the coating composition can be applied to the skin, and preferably up to about 10 layers can be applied.

Any suitable UV light source can be used. For example, a black UV light source, light emitting diode or UV lamp can be used.

Since the coating composition can remain firmly adhered to the skin for one or more days at a time, the method may further include the step of checking the composition coated skin periodically with the UV light source to look for any deterioration of the sunscreen composition particularly in high-contact areas—eg. hands and elbows.

For further protection, the method can include the step of further applying to the skin up to about four layers of a coloured or non-coloured coating composition or a sunscreen composition as described above.

As mentioned above, each of the above skin coating, coloured coating, sunscreen and therapeutic compositions may be formulated for application to the skin, for example, as a paste, cream, gel, solution, liquid, spray or aerosol. The composition may be applied by way of a sponge, brush or spray. The colour, strength, flexibility, plasticity, stability, opacity, viscosity may be readily optimised by adjusting the quantity of each ingredient of the composition. The same coating composition or different coating compositions may be applied to the skin in two or more layers, so as to achieve an optimal effect.

For application by way of a sponge, brush or hand, each composition may be applied neat/undiluted or diluted with diluent up to about a 100% dilution or possibly up to about 233%. For application by way of a spray or aerosol, each composition may be applied after dilution with diluent up to about a 233% dilution (or more). That is, when in a diluted form for application by spray to the skin, for example, each said composition can comprise a ratio of up to about 2.33 parts of alcohol to every 1 part of said composition (70:30 ratio).

The term "comprise" and variants thereof such as "comprising" and "comprised" are used herein to denote the inclusion of a stated integer or integers, unless in the context of usage an exclusive interpretation of a term is required.

Preferred embodiments of the present invention will now be described by way of example with reference to the accompanying figures.

DETAILED DESCRIPTION OF THE EMBODIMENTS

Example 1

Figure 2:
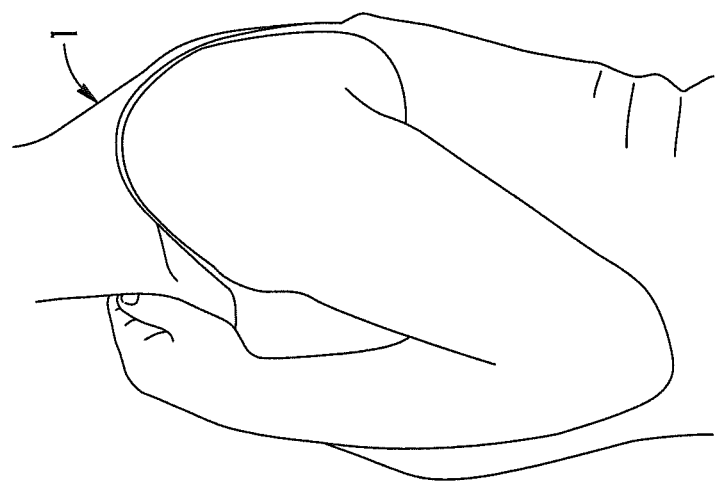
FIG. 2 shows the patient of FIG. 1 treated with a coloured film forming coating composition according to an embodiment of the present invention.

Preparation of a Coloured Film Forming Coating Composition and Use thereof for Coating a Skin Blemish This example describes the preparation of a coloured coating composition and its use in coating a skin blemish such that the blemish has the appearance of normal skin surrounding the blemish. The composition is particularly useful for coating birthmarks, moles, basal cell carcinomas, pigment-related disorders, scars, burns, acne, veins, tattoos, eczema, dermatitis and bruising. The composition can be specifically colour tailored to the needs of an individual.

In order to formulate an appropriate coloured coating composition for coating a skin blemish, several readings of colour (hue, chroma and lightness) were taken from the skin blemish and normal skin surrounding the skin blemish using a spectrophotometer, the procedure for which is described in detail in the applicant's co-pending International Patent Application entitled "A Colour Compensating System". Colour readings were taken from the darkest region of the skin blemish and averaged. Colour readings were also taken from normal skin surrounding the skin blemish and averaged.

A computer database was then interrogated. The computer database contained information relating to the colour properties of the blemish and the colour properties of the skin, as well as information relating to the appropriate colour properties of the coating composition to apply to the blemish such that the coated blemish exhibits the colour of the surrounding skin. The preferred coating compositions have a degree of translucency such that the colour of the coated skin blemish comprises the additive affects of the colour of the coating and the underlying colour of the blemish.

The computer database may be used to select the coating composition. Alternatively, the computer database may provide information as to the desirable colour properties of the coating composition required to obtain the appropriate compensatory colour properties and this information may then be used to provide instructions to the user as to an appropriate coating composition to be prepared to obtain the desired compensatory colour properties.

Once the desired coloured coating composition had been determined, that coating composition was made up from its basic ingredients.

A. Preparation of Primary Pigment and Dye Dispersions

A primary dispersion was made for each pigment and dye to be used in the coloured composition.

Primary dispersions were prepared using one or more of the following pigments and dyes:
  Natural or synthetic iron oxides, black, red, yellow, brown, blended in various ratios.
  Rutile titanium dioxide (micronised).
  Zinc oxide (micronised).
  Ultramarine blue (micronised).
  Mixed metal oxide (cobalt) blue, black, turquoise, green.
  Bon arymadide red pigments.
  Bon red (calcium).
  Rubine toners.
  Arylamide yellows.
  Transparent iron oxide pigments.
  Phthalocyanine blues.
  Dioxazine violets.
  Pearlescent pigments in various colours, including white, copper, bronze.
  Solvent dyes red, orange, yellow, blue, violet, brown, black.

Such pigments and dyes (as well as other suitable pigments and dyes) are available from Redox Chemicals, Polyimpex, Avlo Australia, Clariant Australia, Shepherd International, Merk Australia, Ravenswood Australia, HCA Colours, Degussa Australia, Quantum Chemicals, Multichem, GCI Chemicals Australia, Orica Australia, Tradechem, Johnson and Mathey, Elementis, Bayer Chemicals Pty Ltd, BASF Australia, DIC International, APS Australia, and OMYA Southern.

Each pigment or dye 5-60% w/w was individually mixed to balance with castor oil (to 100% w/w) using a high-speed disperser for approximately 20 minutes, until the pigment or dye was fully wetted.

Each resulting liquid/paste was processed through a bead mill or triple roll mill until a dispersion was achieved of less than 5 micron particle size. Particle size and agglomeration parameters were checked, e.g. using a Hegman guage. Each primary pigment and dye dispersion was then stored in a respective container.

B. Preparation of a Film Forming Composition

Shellac in both solid and liquid form is available from Redox Chemicals, Avlo Australia as well as from Quantum Chemicals. There are many forms of natural shellac available which vary greatly in colour from dark amber to blonde honey colour. A bleached version was used to give minimum coloration to the coloured composition.

De-waxed (blonde) shellac flakes 28% w/w were added slowly to ethanol 55% w/w and stirred until all of the shellac had dissolved. The solution was strained through a 10 micron filter cloth and then the following ingredients were added: ethyl cellulose 4% w/w; castor oil 4% w/w; inorganic thixotrope 4% w/w; preservatives 2% w/w and ethanol to 100% w/w.

A suitable preservative may include, for example, one or more of the following: butylated hydroxytoluene, butylated hydroxyanisole, hydroquinone and methylhydroquinone. Such preservatives may be obtained from Multichem, Redox Chemicals, APS Australia, Quantum Chemicals and Johnson Mathey.

The solution was stirred with gentle heating until all of the solids had dissolved and then strained through a 10 micron filter cloth. The solution was then stored in a container.

C. Preparation of a Blend of Primary Pigment and Dye Dispersions

From the computer/spectrophotometer prediction, select primary pigment and dye dispersions (from part A.) were blended together using a high-speed mixer until homogenous—eg. white ("vehicle") 86.16% w/w, black 03.77% w/w, red 0.58% w/w, yellow ochre 10.88% w/w. A white base (vehicle) was usually prepared from a dispersion of zinc oxide or titanium dioxide.

D. Preparation of a Coloured Film Forming Coating Composition

A final coloured film forming coating composition was then prepared as follows:

| | |
|---|---|
| blend of pigment and dye dispersions (from part C.) | 12% w/w |
| film forming composition (from part B.) | 88% w/w |

The coloured coating composition was mixed vigorously and then applied to skin using brushing, sponging, or airbrushing.

The composition may be readily applied to large skin areas using an airbrush gun. For airbrushing, the final coloured film forming composition 30% volume by volume (v/v) may be diluted in ethanol 70% v/v. The composition is preferably applied to the skin in a cross-hatching manner.

For brushing or sponging, the coloured film forming composition may be used without dilution. A sponge having pores of an appropriate size can produce a stippled effect on the skin. The skin is usually cleaned with soapy water (to remove oils and chemical residues) prior to applying the composition.

Figure 1:
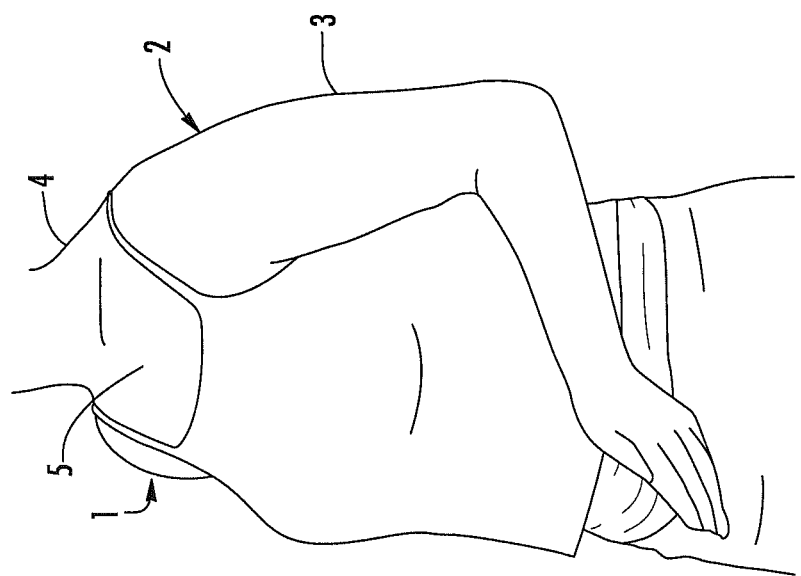
FIG. 1 shows a patient having a port wine stain on her arm.

FIG. 1 shows a patient 1 having a port wine stain 2 extending over her arm 3, neck 4 and chest 5. FIG. 2 shows the same patient 1 but with the port wine stain 2 coated with a coloured composition prepared in accordance with Example 1.

Example 2

Preparation of a Coloured Film Forming Coating Composition and Use thereof for Coating a Skin Blemish This example describes the preparation of another preferred coloured coating composition and its use in coating a skin blemish such that the blemish has the appearance of normal skin surrounding the blemish.

A. Preparation of Primary Pigment and Dye Dispersions

A primary dispersion was made for each pigment and dye to be used in the coloured composition. Primary dispersions were prepared as described in part A. of Example 1 except that the quantity of each pigment or dye varied and was balanced to 100% w/w using triple refined castor oil.

B. Preparation of a Film Forming Composition

A film forming composition was prepared as described in part B. of Example 1 except that the composition comprised:

| | |
|---|---|
| de-waxed (blonde) shellac flakes | 10.37% w/w; |
| ethyl cellulose | 6.10% w/w; |
| castor oil | 13.34% w/w; |
| rosehip oil | 0.99% w/w; |
| BHT | 1.23% w/w; |
| fumed silica | 4.17% w/w; and |
| ethanol | 63.80% w/w. |

C. Preparation of a Blend of Primary Pigment and Dye Dispersions

As described in part C. of Example 1, select primary pigment and dye dispersions (from part A.) were blended together.

D. Preparation of a Coloured Film Forming Coating Composition

A final coloured film forming coating composition was then prepared as follows:

| | |
|---|---|
| blend of pigment and dye dispersions (from part C.) | 12% w/w |
| film forming composition (from part B.) | 88% w/w |

The coloured coating composition was mixed and then applied to skin using brushing, sponging, or airbrushing. For airbrushing, the final coloured film forming composition 30% volume by volume (v/v) may be diluted in ethanol 70% v/v.

Shellac, ethyl cellulose, castor oil and fumed silica are the minimum ingredients required to form the film. Ethanol controls the consistency of the composition and aids application of the composition.

If a matte effect is desired, a fixing powder may be further applied to the coated skin. The fixing powder may be initially applied by sponge immediately after application of the composition and then reapplied after washing the skin. The fixing powder comprised:

| | |
|---|---|
| 92.99% w/w | talc; |
| 4.65% w/w | zinc stearate; |
| 1.43% w/w | silicone oil; and |
| 0.93% w/w | Unigerm G2 ™ (a mixture of methylparaben, ethylparaben, propylene glycol and mydazolidinyl urea). |

Example 3

Preparation of a Film Forming Sunscreen Composition and the Use thereof

This example describes the preparation of a sunscreen composition and the use thereof. The sunscreen composition may protect individuals from premature ageing of skin, skin cancer and other harmful effects of solar radiation. Since the sunscreen film is long-lasting and has a high SPF value, it will be of particular use to those who are exposed to sunlight for long periods of time (e.g. sportsmen).

A. Preparation of a Film Forming Composition

De-waxed (blonde) shellac flakes 28% w/w were added slowly to ethanol 55% w/w and stirred until all of the shellac had dissolved. The solution was strained through a 10 micron filter cloth and then the following ingredients were added: ethyl cellulose 4% w/w; castor oil 4% w/w; inorganic thixotrope 4% w/w; preservatives 2% w/w and ethanol to 100% w/w. The solution was stirred with gentle heating until all of the solids had dissolved and then strained through a 10 micron filter cloth. The solution was stored in a container.

B. Preparation of a Nano Zinc Oxide Dispersion

Inorganic zinc oxide was milled to a nano scale, of less then 100 nm particle size. High energy milling in dry form was used to induce chemical reactions during ball-powder collisions to form nano particles in a solid-state matrix.

Agglomeration was minimized by ensuring that the particles were encapsulated on formation by a solid diluent phase (typically sodium chloride). The solid diluent phase was removed by a basic washing technique. This process formed equiaxed nano particles with a very narrow size distribution and very low levels of agglomeration.

The solid diluent phase allowed the particles to be heat treated without any agglomeration occurring. The heat treatment step ensured the product was completely reacted, removed all residual chemicals and stabilized the surfaces of the particles. The stabilized surfaces assisted in decreasing the reactivity of the particles, which aided in the subsequent dispersion in both aqueous and non-aqueous phases, and limited the generation of free radicals.

Zinc oxide becomes transparent when processed to nano particle size but still retains its UV protection properties. Due to its high refractive indices, zinc oxide blocks UV by both scattering and band gap absorption. A 20-40 nm particle size was selected to provide broad spectrum UVB and UVA protection with maximum transparency in excess of 80%.

Dry milled 20-40 nm zinc oxide (40% w/w) was added slowly to the film forming composition of part A. (60% w/w) and mixed for a minimum of 20 minutes until a homogenous dispersion had been produced. The nano zinc oxide dispersion was then strained through a 10 micron filter cloth and stored in a container.

| Sponge application - single film layer | | | | | | | |
|---|---|---|---|---|---|---|---|
| SPF | SD | UVA Ratio | Range Lower | Range Higher | Star Rating | Category | Critical Wavelength |
| 1.56 | 0.03 | 0.86 | 0.80 | 0.92 | **** | Maximum | 388 nm |

| Application of four film layers/quartz | | | | | | | |
|---|---|---|---|---|---|---|---|
| SPF | SD | UVA Ratio | Range Lower | Range Higher | Star Rating | Category | Critical Wavelength |
| 1216.65 | 630.09 | 0.94 | off scale | off scale | **** | Maximum | 387 nm |

C. Preparation of a Film Forming Sunscreen Composition

A final film-forming sunscreen composition was made up as follows and mixed vigorously before application to the skin:

| | |
|---|---|
| film forming composition (of part A.) | 70% w/w |
| nano zinc oxide dispersion (of part B.) | 30% w/w |

The sunscreen composition was then applied using brushing, sponging, or airbrushing.

Example 4

Sun Protection Factor Value of a Sunscreen Composition Containing Micronised Zinc Oxide A coloured coating composition was prepared in accordance with Example 1 and had the colour blend: blue 0.60% w/w; red 0.53% w/w; yellow ochre 11.25% w/w; and white (vehicle) 47.60% w/w. Since the vehicle comprised micronised zinc oxide, the coloured coating composition also functioned as a sunscreen.

The composition was analysed using a Labsphere SPF Analyser with the following parameters:

substrate: MimSkin® on quartz film thickness: 2 mg/cm$^2$ number of scans: 10

UVB/UVA cut off: 320 nm

The results are summarised in the following tables:

| Brush application - single film layer | | | | | | | |
|---|---|---|---|---|---|---|---|
| SPF | SD | UVA Ratio | Range Lower | Range Higher | Star Rating | Category | Critical Wavelength |
| 2.10 | 0.12 | 0.92 | off scale | off scale | **** | Maximum | 388 nm |

Figure 3:
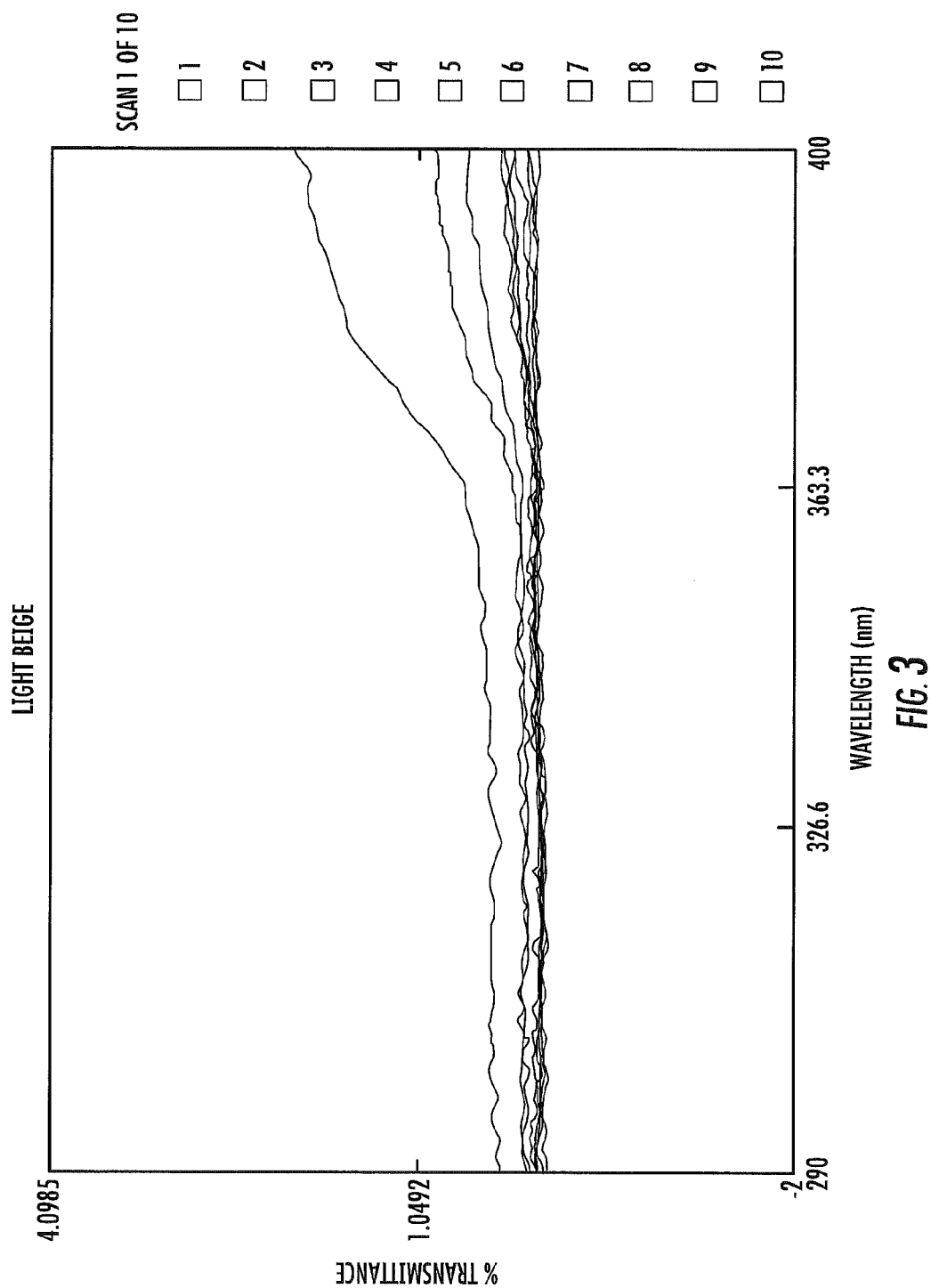
FIG. 3 is a plot of percentage transmittance versus wavelength for a coloured film forming coating/sunscreen composition, according to an embodiment of the present invention.

The final table shows that multilayering the film on skin (four layers) is likely to provide a much higher SPF value, in this case being 1216.65. FIG. 3 is a plot of percentage transmittance versus wavelength for the composition when applied as four layers, and indicates that the composition can provide broad UV protection.

Example 5

Preparation of a Film Forming Therapeutic Sunscreen Composition

This example describes the preparation of a preferred therapeutic sunscreen composition.

A film forming composition was prepared as described in parts A., B. and C. of Example 3 except that the final composition comprised:

| | |
|---|---|
| de-waxed (blonde) shellac flakes | 12.96% w/w; |
| ethyl cellulose | 7.79% w/w; |
| castor oil | 1.14% w/w; |
| rosehip oil | 0.50% w/w; |
| BHT | 1.00% w/w; |
| vitamin E acetate | 0.50% w/w; |
| nano zinc oxide | 34.40%; and |
| ethanol | 41.44% w/w. |

Shellac, ethyl cellulose, castor oil and nano zinc oxide are the minimum ingredients required to form the film. Ethanol controls the consistency of the composition and aids application of the composition.

The composition contains the therapeutic agent vitamin E acetate. This agent is an antioxidant and can decrease the effects of psoriasis, erythema and scarring from wounds. If desired, other therapeutic agents (eg. growth factors, steroids, antiseptics, antibacterials) may be used in the composition.

Example 6

Sun Protection Factor Value of a Sunscreen Composition Containing Nano Zinc Oxide The therapeutic composition of Example 5 was analysed using a Labsphere SPF Analyser with the following parameters:

substrate: MimSkin® on quartz rub-in method film thickness: 2 mg/cm$^2$ number of scans: 10

UVB/UVA cut off: 320 nm

The results are summarised in the following tables:

| Pre photodegradation |||||||||
| --- | --- | --- | --- | --- | --- | --- | --- |
| SPF | SD | UVA Ratio | Range Lower | Range Higher | Star Rating | Category | Critical Wavelength |
| 11.68 | 1.32 | 0.82 | 0.77 | 0.88 | ***** | Ultra | 377 nm |

| Post photodegradation |||||||||
| --- | --- | --- | --- | --- | --- | --- | --- | --- |
| SPF | SD | UVA Ratio | Range Lower | Range Higher | Star Rating | Category | Photo-stability | Critical Wavelength |
| 11.32 | 1.62 | 0.82 | 0.77 | 0.88 | ***** | Ultra | Yes | 377 nm |

Figure 4:
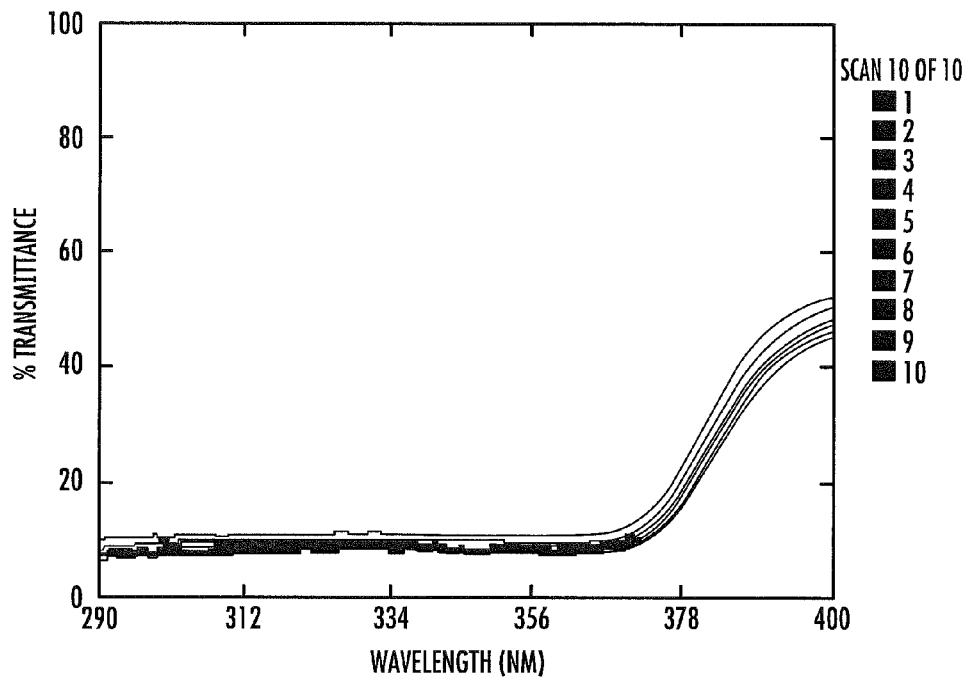
FIG. 4 is a plot of percentage transmittance versus wavelength for a sunscreen composition, according to an embodiment of the present invention.
Figure 5:
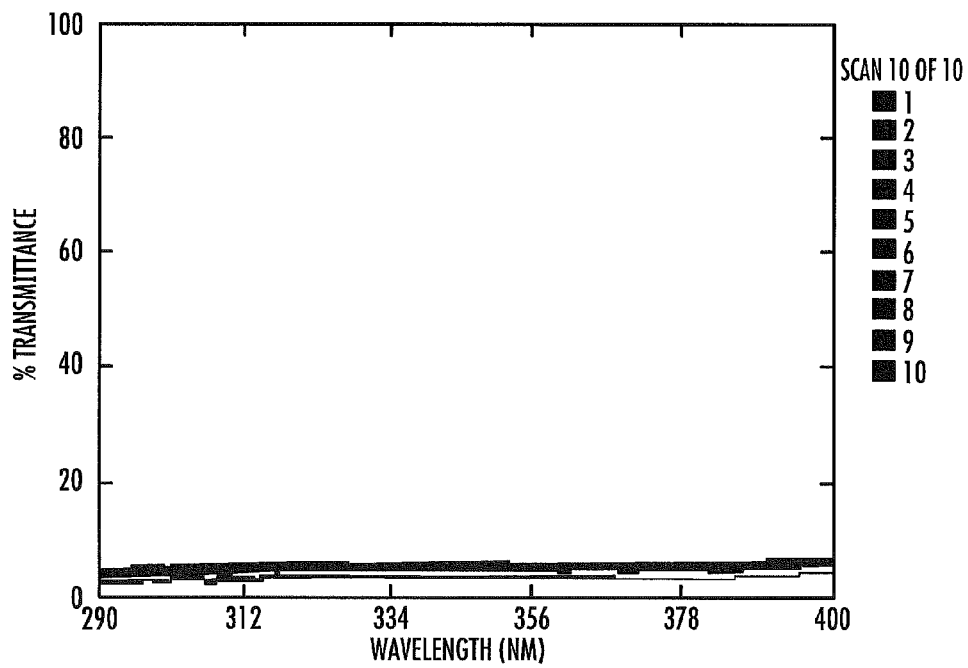
FIGS. 5 to 8 are plots of percentage transmittance versus wavelength for a coloured film forming coating/sunscreen composition, according to an embodiment of the present invention.
Figure 6:
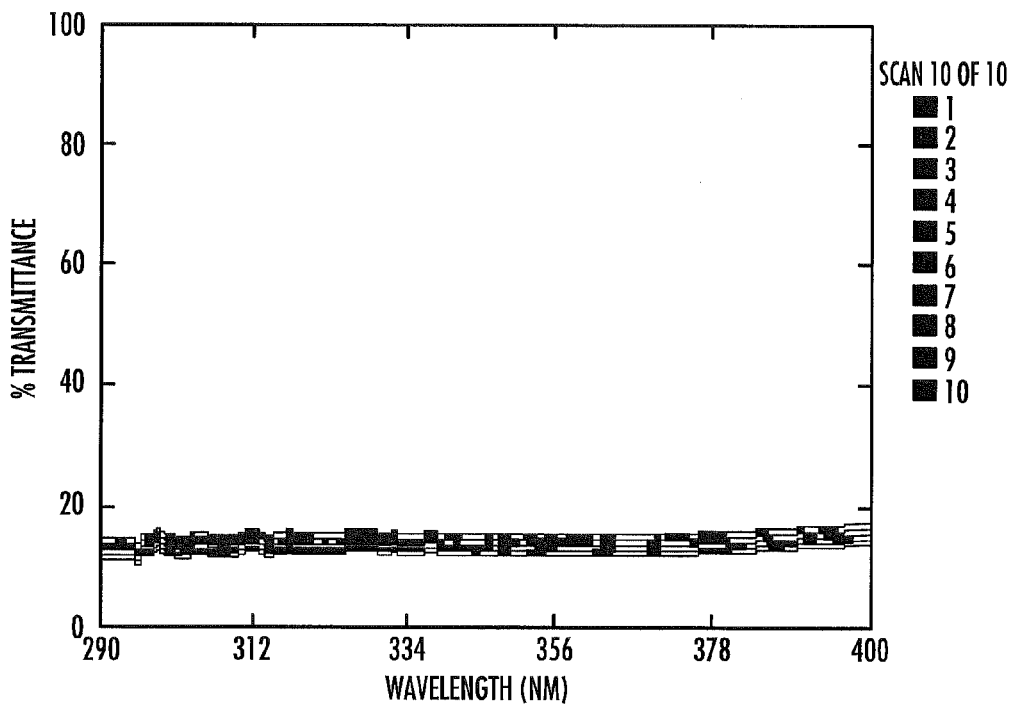
Figure 7:
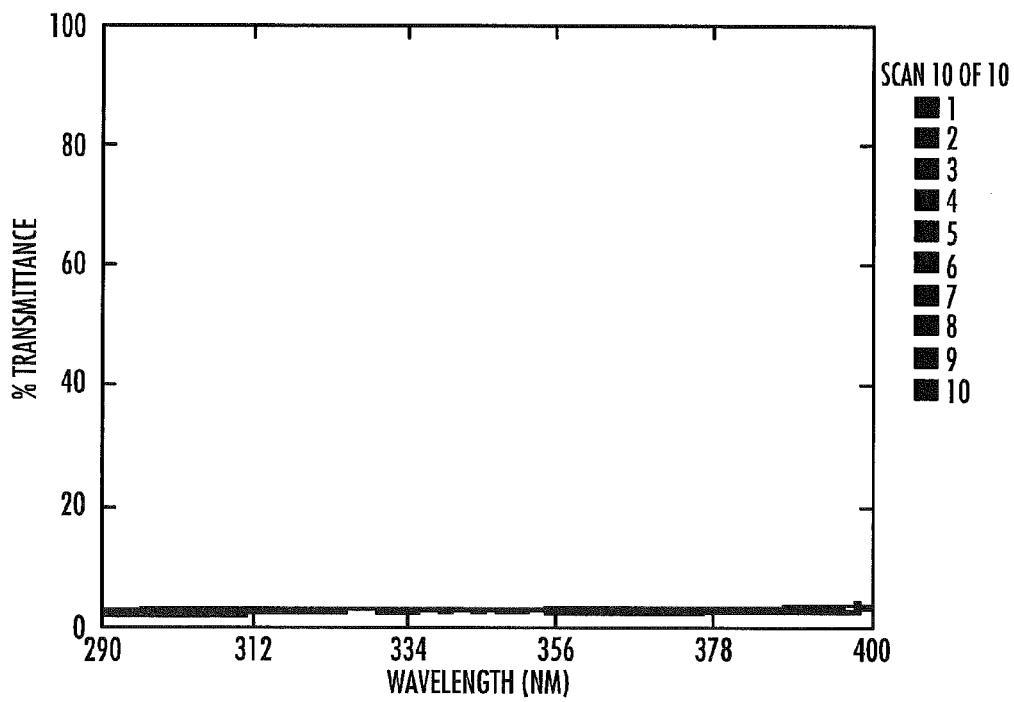
Figure 8:
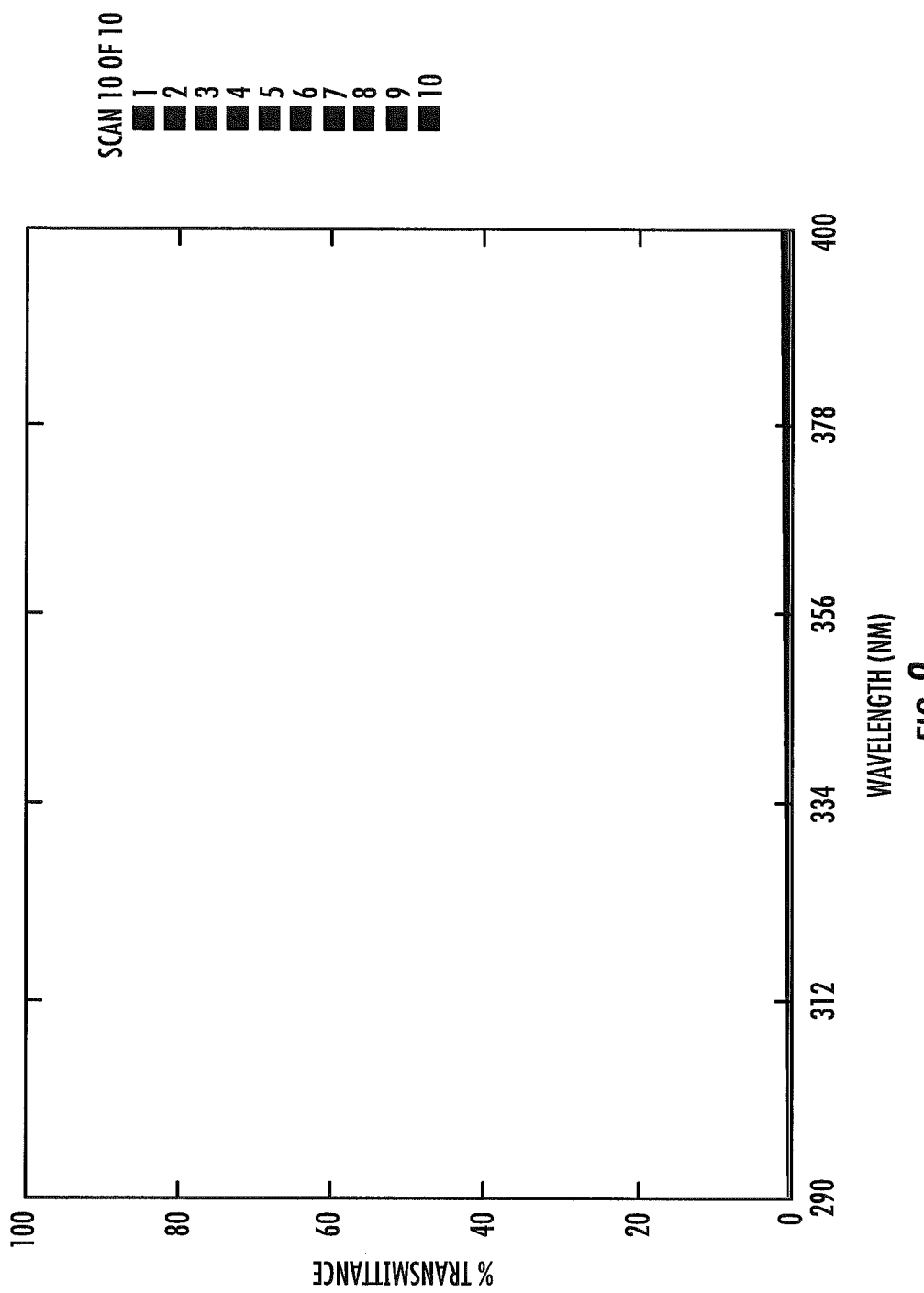

FIG. 4 is a plot of percentage transmittance versus wavelength for the composition when applied as a single layer. As for the composition tested in Example 4, multilayering the film on skin (four layers) provided a much higher (and more than additive) SPF value, and provided broad UV protection (results not shown).

Example 7

Sun Protection Factor Value of a Coloured Sunscreen Composition

A coloured coating composition was prepared in accordance with Example 2.

Each of the following primary dispersions was prepared (to 100% w/w balance with castor oil):

| | |
| --- | --- |
| black iron oxide (Elementis) | 25% w/w |
| rubine bright red (Polyimpex) | 20% w/w |
| white (Tronox ® CR-828 titanium dioxide) | 50% w/w |
| yellow ochre | 40% w/w |

The following primary dispersion quantities were mixed with 44 g of the film forming composition described in part B. of Example 2: 0.03 g black iron oxide; 0.07 g rubine bright red; 4.13 g white; and 1.48 g yellow ochre.

Since the composition contained titanium dioxide, the coloured coating composition could also function as a sunscreen.

The composition, applied in 1 to 4 layers, was analysed using a Labsphere SPF

Analyser with the following parameters:

substrate: MimSkin® on quartz rub-in method film thickness: 2 mg/cm$^2$ number of scans: 10

UVB/UVA cut off: 320 nm

The results are summarised in the following tables:

| Spray application - single film layer |||||||
| --- | --- | --- | --- | --- | --- | --- |
| SPF | SD | UVA Ratio | Range Lower | Range Higher | Star Rating | Category | Critical Wavelength |
| 7.2 | 0.61 | 0.98 | Too high | Too high | ***** | Ultra | 389 nm |

| Spray Application - two film layers |||||||||
| --- | --- | --- | --- | --- | --- | --- | --- | --- |
| SPF | SD | UVA Ratio | Range Lower | Range Higher | Star Rating | Category | Photo-stability | Critical Wavelength |
| 19.6 | 3.06 | 0.98 | Too high | Too high | ***** | Ultra | Yes | 389 nm |

| Spray Application - three film layers |||||||||
| --- | --- | --- | --- | --- | --- | --- | --- | --- |
| SPF | SD | UVA Ratio | Range Lower | Range Higher | Star Rating | Category | Photo-stability | Critical Wavelength |
| 53.42 | 11.98 | 0.98 | Too high | Too high | ***** | Ultra | Yes | 389 nm |

| | | Spray Application - four film layers | | | | | |
|---|---|---|---|---|---|---|---|
| SPF | SD | UVA Ratio | Range Lower | Range Higher | Star Rating | Category | Photo-stability | Critical Wavelength |
| 115.21 | 21.74 | 0.98 | Too high | Too high | ***** | Ultra | Yes | 389 nm |

The final table shows that multilayering the film on skin (four layers) is likely to provide a much higher SPF value, in this case being 115.21. FIGS. 5-8 are plots of percentage transmittance versus wavelength for the composition when applied as one to four layers, respectively, and indicate that the composition can provide broad UV protection.

Example 8

Preparation of Other Coloured Film Forming Coating Compositions and Use thereof for Coating a Skin Blemish This example describes the preparation of other preferred coloured coating compositions for use in coating a skin blemish such that the blemish has the appearance of normal skin surrounding the blemish.

This example describes both concentrated and diluted forms of coloured coating compositions as well as their preferred uses.

A. Preparation of Primary Pigment and Dye Dispersions

A primary dispersion was made for each pigment and dye to be used in the coloured composition. Primary dispersions were prepared as described in part A. of Example 1 except that the quantity of each pigment or dye varied and was balanced to 100% w/w using castor oil. The final pigment or dye concentration was either 60% w/w or 40% w/w.

B. Preparation of a Film Forming Composition

A film forming composition was prepared as described in part B. of Example 1 except that the composition comprised:

| | |
|---|---|
| de-waxed (blonde) shellac flakes | 8.5% w/w; |
| ethyl cellulose | 9.0% w/w; |
| castor oil | 18.0% w/w; |
| BHT | 2.0% w/w; |
| fumed silica | 3.5% w/w; |
| SAIB | 0.2% w/w; and |
| ethanol | balance to 100% w/w. |

C. Preparation of a Blend of Primary Pigment and Dye Dispersions

As described in part C. of Example 1, select primary pigment and dye dispersions (from part A.) were blended together.

D. Preparation of a Coloured Film Forming Coating Composition

A final coloured film forming coating composition was then prepared as follows:

| | |
|---|---|
| blend of pigment and dye dispersions (from part C.) | 15.0% w/w |
| film forming composition (from part B.) | 85.0% w/w |

Both undiluted and 233% diluted coloured compositions (but not showing % preservative, which is an optional ingredient) are shown in Tables 1 and 2 below:

TABLE 1

Coloured Composition Prepared From Pigment Concentration 60% w/w

| INGREDIENT | UNDILUTED COLOURED COMPOSITION* (% w/w) | DILUTION 30:70 COLOURED COMPOSITION:ALCOHOL (% w/w) | EXPECTED WORKING RANGE OF INGREDIENT (% w/w) |
|---|---|---|---|
| Resin/Natural gum derivative - Shellac | 4.04 | 1.21 | 1-30% |
| Alcohol - Ethanol | 52.54 | 85.76 | 40-90% |
| Oil - Castor oil | 25.54 | 7.66 | 2-70% |
| Cellulosic preparation - Ethyl cellulose | 5.74 | 1.72 | 0.5-10% |
| Inorganic thickener - fumed silica (Aerosil COK84) | 1.88 | 0.56 | 0.1-10% |
| Pigment/Dye | 9.09 | 2.73 | Up to 5.5% |

TABLE 2

Coloured Composition Prepared From Pigment Concentration 40% w/w

| INGREDIENT | UNDILUTED COLOURED COMPOSITION* (% w/w) | DILUTION 30:70 COLOURED COMPOSITION:ALCOHOL (% w/w) | EXPECTED WORKING RANGE OF INGREDIENT (% w/w) |
|---|---|---|---|
| Resin/Natural gum derivative - Shellac | 4.03 | 1.21 | 1-30% |
| Alcohol - Ethanol | 55.64 | 86.70 | 40-90% |
| Oil - Castor oil | 25.54 | 7.66 | 2-70% |
| Cellulosic preparation - Ethyl cellulose | 5.74 | 1.72 | 0.5-10% |
| Inorganic thickener - fumed silica (Aerosil COK84) | 1.88 | 0.56 | 0.1-10% |
| Pigment/Dye | 6.00 | 1.80 | Up to 5.5% |

Based on the compositions prepared to date, it is expected that the working ranges for ingredients in both non-coloured and coloured film-forming compositions (both with and without additional sunscreen and therapeutic agents) are likely to be approximately as follows:
- 1-30% w/w substantially alcohol soluble resin/natural gum derivative as a film-former and waterproofing agent;
- 40-90% w/w primary alcohol as a diluent and viscosity modifier;
- 2-70% w/w non-drying or semi-drying oil as a film-former and flexibilizer;
- 0.5-10% w/w cellulosic preparation as a flexibilizer and/or adhesive; and
- 0.1-10% w/w inorganic thickener.

It is to be understood, however, that in some instances for some ingredients the actual amounts may sometimes lay outside of the working ranges shown in the tables above.

Examples and uses of the coloured composition* at different dilution ratios are described below:

Example A

Undiluted Coloured Composition*

| | |
|---|---|
| Coloured composition* | 100 parts by weight (pbw) |
| Alcohol diluent | 0 pbw |

The coloured composition* in an undiluted form is applied by the user for quick thick coverage of a significant skin blemish, usually by brushing or sponging.

Example B

43% Dilution (70:30 Ratio)

| | |
|---|---|
| Coloured composition* | 100 pbw |
| Alcohol diluent | 43 pbw |

The coloured composition can be used in this diluted form for quick coverage of the bulk area of significant skin blemishes without a thick layer of applied coating. This diluted form permits (spray) application to the main areas of (large) skin blemishes to give coverage without excessively thick film application which detracts from "skin feel".

Example C

100% Dilution (50:50 Ratio)

| | |
|---|---|
| Coloured composition* | 100 pbw |
| Alcohol diluent | 100 pbw |

The coloured composition can be used in this diluted form to give a lower colour concentration intensity than in Example B, to permit better control in the application of (spray) application to toning of the main areas of (large) skin blemishes with the surrounding normal skin. That is, it allows the wearer to tone in the fringe areas of the coated skin blemish to blend in with the surrounding normal skin.

Example D

233% Dilution (30:70 Ratio)

| | |
|---|---|
| Coloured composition* | 100 pbw |
| Alcohol diluent | 233 pbw |

The coloured composition can be used in this diluted form to permit spray application, or "packaging" in individual containers for ready-for-use "local field touch-ups" of above Examples B and C.

A range of prepackaged coloured compositions having specific pre-selected pigment/dye mixes can be made available to consumers with a skin tone reference chart. After consulting the reference chart, consumers may select a prepackaged composition based on their skin tone in order to coat a blemish (or other defect of the skin) and give that blemish a more natural appearance. Of course, a reference computer database as described in Example 1 above and in the applicant's co-pending International Patent Application entitled "A Colour Compensating System" can be consulted instead of a skin tone reference chart.

Example 9

Preparation of a Skin Tone-based Film Forming Sunscreen Composition and the Testing thereof This example describes the preparation of a skin-toned sunscreen composition that provides the wearer with a toned appearance and the testing thereof.

A. Preparation of Film Forming Composition

De-waxed (blonde) shellac flakes 8.5% w/w were added slowly to ethanol 61.0% w/w and stirred until all of the shellac had dissolved. The solution was strained through a 10 micron filter cloth and then the following ingredients were added: ethyl cellulose 9.0% w/w; castor oil 18.0% w/w; inorganic thixotrope 3.5% w/w; preservatives 2.0% w/w and ethanol to 100% w/w. The solution was stirred with gentle heating until all of the solids had dissolved and then strained through a 10 micron filter cloth. The solution was stored in a container.

B. Preparation of a Zinc Oxide Dispersion

Inorganic zinc oxide was prepared as described for Example 3. Briefly, milled 20-40 nm zinc oxide (40% w/w) was added slowly to the film forming composition of part A. (60% w/w) and mixed for a minimum of 20 minutes until a homogenous dispersion had been produced.

C. Preparation of a Skin Tone-based Film Forming Sunscreen Composition

A final film-forming sunscreen composition was made up as follows and mixed vigorously before application to the skin:

| | |
|---|---|
| film forming composition (of part A.) | 35% w/w |
| zinc oxide dispersion (of part B.) | 48% w/w |
| blend of pigment and dye dispersion (from Example 8, part C.) | 17% w/w |

Following dilution in ethanol as in Example 8, the sunscreen composition was applied by airbrushing (spray) to the substrate in one, two or three layers. The effectiveness of spraying was compared with routine application using a finger stall at a 50 g (light) application to the substrate. Evaluation of both photostability and water resistance was also undertaken.

The composition was analysed using a Labsphere Transmittance Analyser with the following parameters:
substrate: MimSkin® on quartz
film thickness: 2 mg/cm² coverage=17 mg
wavelength: 290-400 nm The following three tables summarise the effect of layering (×3) the composition by spray on SPF.

| Spray application - single film layer (6 mg) | | | | | |
|---|---|---|---|---|---|
| SPF mean (6 scans) | SD | UVA/UVB Ratio | Star Rating | Category | Critical Wavelength |
| 6.08 | 0.39 | 0.98 | ***** | Ultra | 388 nm |

| Spray application - two film layers (14 mg/20 mg total) | | | | | |
|---|---|---|---|---|---|
| SPF mean (6 scans) | SD | UVA/UVB Ratio | Star Rating | Category | Critical Wavelength |
| 122.89 | 21.63 | 0.97 | ***** | Ultra | 388 nm |

| Spray Application - three film layers (3 mg/23 mg total) | | | | | |
|---|---|---|---|---|---|
| SPF mean (6 scans) | SD | UVA/UVB Ratio | Star Rating | Category | Critical Wavelength |
| 500 | 0 | 0.95 | ***** | Ultra | 388 nm |

| Routine application using a finger stall - single layer 17 mg dry | | | | | |
|---|---|---|---|---|---|
| SPF mean (10 scans) | SD | UVA/UVB Ratio | Star Rating | Category | Critical Wavelength |
| 10.92 | 0.66 | 0.98 | ***** | Ultra | 389 nm |

Multilayering the film on skin (three layers) by spray provided a much higher (and more than additive) SPF value, and provided broad UV protection.

Example 10

Preparation of a White-based Film Forming Sunscreen Composition and the Testing thereof This example describes the preparation of a white-based sunscreen composition and the testing thereof for sun protection.

A. Preparation of a Film Forming Composition

De-waxed (blonde) shellac flakes 8.5% w/w were added slowly to ethanol 61.0% w/w and stirred until all of the shellac had dissolved. The solution was strained through a 10 micron filter cloth and then the following ingredients were added: ethyl cellulose 9.0% w/w; castor oil 18.0% w/w; inorganic thixotrope 3.5% w/w; preservatives (BHT) 2.0% w/w and ethanol to 100% w/w. The solution was stirred with gentle heating until all of the solids had dissolved and then strained through a 10 micron filter cloth. The solution was stored in a container.

B. Preparation of a Zinc Oxide Dispersion

Inorganic zinc oxide was prepared as described for Example 3. Briefly, milled 400-1000 nm zinc oxide (40% w/w) was added slowly to the film forming composition of part A. (60% w/w) and mixed for a minimum of 20 minutes until a homogenous dispersion had been produced.

C. Preparation of a White-based Film Forming Sunscreen Composition

A final film-forming sunscreen composition was made up as follows and mixed vigorously before application to the skin:

| | |
|---|---|
| film forming composition (of part A.) | 52% w/w |
| zinc oxide dispersion (of part B.) | 48% w/w |

Following dilution in ethanol as in Example 8, the sunscreen composition was applied by airbrushing (spray) to the substrate in one or two layers. Evaluation of both photostability and water resistance was undertaken.

The composition was analysed using a Labsphere Transmittance Analyser with the following parameters:

substrate: MimSkin® on quartz film thickness: 2 mg/cm² coverage=17 mg wavelength: 290-400 nm The following tables summarise the effect of layering (×2) the composition by spray on SPF.

| Spray application - single film layer | | | | | |
|---|---|---|---|---|---|
| SPF mean (10 scans) | SD | UVA/UVB Ratio | Star Rating | Category | Critical Wavelength |
| 14.52 | 1.28 | 0.85 | **** | Superior | 379 nm |

| Spray application - two film layers (20 mg total) | | | | | |
|---|---|---|---|---|---|
| SPF mean (10 scans) | SD | UVA/UVB Ratio | Star Rating | Category | Critical Wavelength |
| 420.34 | 46.75 | 0.88 | **** | Superior | 378 nm |

Again, the tables show that multilayering the film on skin is likely to provide a much higher SPF value.

The following tables summarise the water resistance of the composition (in a controlled spa) after 30 minutes, 1 hour or 4 hours with the temperature raised to 37 degrees celsius for the last 2 hours.

| Spray application single layer - post 30 minute water immersion - single layer | | | | | |
|---|---|---|---|---|---|
| SPF mean (10 scans) | SD | UVA/UVB Ratio | Star Rating | Category | Critical Wavelength |
| 19.8 | 3.31 | 0.85 | **** | Superior | 378 nm |

| Spray application single layer - post 1 hour water immersion | | | | | |
|---|---|---|---|---|---|
| SPF mean (10 scans) | SD | UVA/UVB Ratio | Star Rating | Category | Critical Wavelength |
| 18.32 | 3.69 | 0.83 | **** | Superior | 378 nm |

| Spray application single layer - post 1 hour water immersion plus UV exposure at SPF 31 | | | | | |
|---|---|---|---|---|---|
| SPF mean (10 scans) | SD | UVA/UVB Ratio | Star Rating | Category | Critical Wavelength |
| 20.75 | 3.96 | 0.82 | **** | Superior | 378 nm |

| Spray application single layer - post 4 hours water immersion with the temperature raised to 37 degrees celsius for the last 2 hours | | | | | |
|---|---|---|---|---|---|
| SPF mean (10 scans) | SD | UVA/UVB Ratio | Star Rating | Category | Critical Wavelength |
| 17.71 | 2.23 | 0.84 | **** | Superior | 379 nm |

If desired, the compositions of Examples 9 and 10 can contain one or more anti-causative agents such as Uvinul A Plus, Uvinul T 150 and Uvinul MC 80.

Examples 9 and 10 as well as additional testing (results not shown) illustrate that the compositions are:

highly protective (SPF>100), where SPF is not a linear function of application rate:
  very light application SPF<6
  light application SPF 6-15
  moderate application SPF 15-50
  strong application (equivalent to standard sunscreen) SPF 50->100
very highly water proof, not merely resistant
sweat proof, not merely resistant
very rapid dry-off
highly substantive—cannot be removed by washing, (sc) rubbing toweling
no re-application required
high UVA/B absorbance ratio
non-irritant
non allergenic
non staining
photostable
comfortable to wear
easily and completely removed with formulated serum
UVA Ratio>0.95 for skin tone-based composition
UVA Ratio>0.80 for white (zinc oxide) based composition
white (zinc oxide) based composition—skin lightening (for the Asian Market)
best sprayed for high SPF.

Example 11

Preparation of a White-based Film Forming Sunscreen Composition

This example describes a white-based sunscreen composition like that of Example 10 but further with UV-A and UV-B agents to further boost SPF protection and to provide other advantages.

A. Preparation of a Film Forming Composition

De-waxed (blonde) shellac flakes 8.5% w/w were added slowly to ethanol 61.0% w/w and stirred until all of the shellac had dissolved. The solution was strained through a 10 micron filter cloth and then the following ingredients were added: ethyl cellulose 9.0% w/w; castor oil 18.0% w/w; inorganic thixotrope 3.5% w/w; preservatives (BHT) 2.0% w/w and ethanol to 100% w/w. The solution was stirred with gentle heating until all of the solids had dissolved and then strained through a 10 micron filter cloth. The solution was stored in a container.

B. Preparation of a Zinc Oxide Dispersion

Inorganic zinc oxide was prepared as described for Example 10, part B. Briefly, milled 400-1000 nm zinc oxide (40% w/w) was added slowly to the film forming composition of part A. (60% w/w) and mixed for a minimum of 20 minutes until a homogenous dispersion had been produced.

C. Preparation of a White-based Film Forming Sunscreen Composition

A final film-forming sunscreen composition was made up as follows and mixed vigorously before application to the skin:

| | |
|---|---|
| film forming composition (of part A.) | 44% w/w |
| zinc oxide dispersion (of part B.) | 50% w/w |
| UV-A agent | 2.5% w/w |
| UV-B agent | 3.5% w/w |

The UV-A agent is preferably Uvinul A Plus™ from BASF and the UV-B agent is preferably Uvinul MC80™ from BASF, although other anti-causative agents could be used.

Following dilution in ethanol as in Example 8, the sunscreen composition was applied (preferably by spray application) to the person.

This form of sunscreen may be applied preemptively, for long term safeguarding against premature skin aging and perhaps cancer. Whilst the zinc oxide prevents the immediate effects of sun damage (ie. skin reddening, first and second degree burns), the anti-causative agents hinder premature skin aging effects (photo aging) of the skin due to free radical actions. The Uvinul™ mops up free radicals that are generated by sunlight (predominately UV-A and UV-B rays) which degrades the sub-layers of the skin and results in premature aging appearance of the skin and possible skin cancer.

Example 12

Preparation of a Pigmented Film Forming Sunscreen Composition

This example describes a sunscreen composition like that of Example 11 but giving the wearer a bronzed appearance.

A. Preparation of Film Forming Composition

A film-forming composition was prepared as described for Example 11—de-waxed (blonde) shellac flakes 8.5% w/w; ethyl cellulose 9.0% w/w; castor oil 18.0% w/w; inorganic thixotrope 3.5% w/w; preservatives 2.0% w/w and ethanol to 100% w/w.

B. Preparation of a Zinc Oxide Dispersion

Inorganic zinc oxide was prepared as described for Example 11.

C. Preparation of Primary Pigment and Dye Dispersions, and Blend

A primary dispersion was made for each pigment and dye to be used in the coloured composition. Primary dispersions were prepared as described in part A. of Example 1 except that the quantity of each pigment or dye varied and was balanced to 100% w/w using castor oil.

As largely described in part C. of Example 1, the following select primary pigment and dye dispersions were blended together:

| | |
|---|---|
| Red | 13.8 g |
| Yellow Oxide | 50.6 g |
| Brown | 45.6 g |
| TOTAL | 110 g. |

D. Preparation of a Bronze Coloured Film Forming Sunscreen Composition

A final film-forming sunscreen composition was made up as follows and mixed vigorously before application to the skin:

| | |
|---|---|
| film forming composition (of part A.) | 33% w/w |
| zinc oxide dispersion (of part B.) | 50% w/w |
| blend of pigment and dye dispersion (of part C.) | 17% w/w |

The final film-forming sunscreen composition can optionally include additional UV-A and UV-B agents such as, for example, Uvinul A Plus™ 3.5% w/w, Uvinul MC 80™ 3.1% w/w and Uvinul T 150™ 1.0% w/w, in which case the film forming composition (of part A.) is reduced to 28% w/w and the blend of pigment and dye dispersion (of part C.) is reduced to 14.4% w/w.

Following dilution in ethanol as in Example 8, the sunscreen composition was applied by airbrushing (spray) to the substrate in one, two or three layers.

Example 13

Method of Coating the Skin of Individuals with Xeroderma Pigmentosum or Other Sun-sensitive Skin Conditions This example describes how individuals with Xeroderma Pigmentosum (XP) or with other sun-sensitive skin conditions can have their skin effectively shielded against harmful UV radiation.

A fluorophore carrier composition was prepared and applied to the skin of the XP individual. The fluorophore carrier composition comprised fluorophore DGS-00 (Dayglow Colour Corp.) 5% w/w plus 95% w/w of a non-pigmented film forming composition, as shown below:

| | |
|---|---|
| dewaxed blonde shellac | 7.8% w/w |
| ethyl cellulose | 8.8% w/w |
| castor oil | 15.8% w/w |
| BHT | 1.8% w/w |
| fumed silica | 2.9% w/w |

| | |
|---|---|
| SAIB | 0.3% w/w |
| fluorophore powder | 5.0% w/w |
| ethanol | to 100% w/w |

Following dilution in ethanol as in Example 8, the fluorophore carrier composition was evenly spray-applied to the skin of the XP individual using a standardized procedure—a measured amount per square inch of the exposed skin area. Following application, a black UV light source was passed over the skin (3-5 seconds per scan) to make sure that there was even coverage.

Up to ten layers of a coloured film forming coating composition as described in Example 8 was then spray-applied to the XP individual's skin. After application, fixing powder as described in Example 2 could be applied to render the skin feel less sticky.

Once the coloured film forming coating composition had been applied, a black UV light source was passed over the skin to see if there was any fluorescence due to uncoated fluorophore. If so, this would mean that at least one further layer of composition would need to be applied to the skin of the XP individual.

For further protection, up to four further layers of the sunscreen composition as described in Example 10 could be applied, following the application of fixing powder, if desired.

Although the coloured film forming coating composition and sunscreen composition can remain firmly adhered to the skin for one or more days at a time, the skin should be checked periodically with the light source to look for any deterioration of the composition in high-contact areas—eg. hands and elbows.

The coating compositions as broadly exemplified in the examples have one or more of the following advantages:
- they are flexible and durable on the skin (typically lasting between 1 to 5 days);
- they may be multilayered to provide a superior effect;
- they are waterproof and sweat proof;
- they remain intact even when immersed in hot water;
- they bond to the skin when immersed in saltwater;
- they remain intact even if clothing or a shaver is scraped over the film
- they help keep the skin sterile;
- they do not cause skin blemishes (pimples, breakouts);
- they are gentle to the skin; and
- they are easy to apply to the skin.

Whilst the above has been given by way of illustrative example of the invention, many modifications and variations may be made thereto by persons skilled in the art without departing from the broad scope and ambit of the invention as herein set forth.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A coating composition suitable for use on skin, said composition comprising:
    about 5 to 30% w/w resin;
    about 50 to 80% w/w alcohol;
    about 7 to 42.5% w/w oil;
    about 2 to 10% w/w cellulosic preparation; and
    about 0.5 to 10% w/w inorganic thickener,
    wherein the ratio of resin to oil to cellulosic preparation ranges from 0.5:0.7:1 to 15:21.25:1, and wherein the resin is shellac, the alcohol is ethanol, the oil is castor oil or a mixture of castor oil and rosehip oil, the cellulosic preparation is ethyl cellulose, and the inorganic thickener is silicon dioxide.

2. A coating composition suitable for use on skin, said composition comprising
    about 5 to 30% w/w resin;
    about 50 to 80% w/w alcohol;
    about 7.1 to 42.5% w/w oil;
    about 2 to 10% w/w cellulosic preparation; and
    about 0.5 to 10% w/w inorganic thickener,
    wherein the ratio of resin to oil to cellulosic preparation ranges from 0.5:0.7:1 to 15:21.25:1, and wherein the resin is shellac, the alcohol is ethanol, the oil is a mixture of 7 to 42.4% w/w castor oil and 0.1 to 5% w/w rosehip oil, and the oil in a range of about 7 to 42.5% w/w, the cellulosic preparation is ethyl cellulose, and the inorganic thickener is silicon dioxide.

3. The coating composition of claim 1, wherein the coating composition further comprises at least one pigment and/or dye.

4. The coating composition of claim 3, wherein the coating composition comprises about 0.01 to 10% w/w pigment and/or dye.

5. A diluted coating composition suitable for use on skin comprising 30% volume by volume (v/v) of the composition of claim 4 and 70% v/v ethanol.

6. The coating composition of claim 1, wherein the coating composition further comprises at least one sunscreen agent.

7. The coating composition of claim 6, wherein the coating composition comprises about 10 to 60% w/w sunscreen agent.

8. The coating composition of claim 7, wherein the sunscreen agent comprises zinc oxide.

9. The coating composition of claim 6, wherein the resin is shellac, the alcohol is ethanol, the oil is a mixture of 7 to 15% w/w castor oil and 0.1 to 5% w/w rosehip oil, the cellulosic preparation is ethyl cellulose, and the sunscreen agent is zinc oxide having a particle size of between about 5 to 100 nm.

10. The coating composition of claim 6, wherein the coating composition further comprises at least one therapeutic agent.

11. The coating composition of claim 10, wherein the therapeutic agent comprises about 0.5 to 5% w/w vitamin E acetate.

12. A method of preparing a waterproof flexible colored film for coating a skin discoloration or skin blemish comprising using a coating composition according to claim 3 in the formation of the waterproof flexible colored film, wherein said coating composition comprising an effective amount of at least one pigment and/or dye, such that, upon application to the skin, said composition forms the waterproof flexible colored film over the skin discoloration or blemish so that the skin discoloration or blemish blends with the surrounding skin.

13. The method of claim 12, wherein said coating composition further comprises a sunscreen agent and/or a therapeutic agent.

14. The method of claim 12, wherein the skin discoloration or blemish is selected from the group consisting of a birthmark, a mole, a basal cell carcinoma, vitiligo, a scar, a burn, pigmentation, acne, a vein, tattoo, eczema, dermatitis and bruising.

15. The method of claim 12, wherein the coating composition is formulated to enable the use of a fixing powder on the coated skin discoloration or blemish.

16. The method of claim 15, wherein the fixing powder comprises:
about 93.0% w/w talc;
about 4.7% w/w zinc stearate;
about 1.4% w/w silicone oil; and
about 0.9% w/w preservative.

17. The method of claim 12, wherein the coating composition is formulated as a paste.

18. The method of claim 12, wherein the coating composition of claim 3 is formulated for dilution in ethanol prior to use to produce a composition having 30% volume by volume (v/v) of the coating composition and 70% v/v ethanol and wherein the diluted coated composition is suitable for administration to the skin by spraying.

19. A method of preparing a waterproof flexible film comprising using a coating composition according to claim 6 in the preparation of the waterproof flexible film, wherein said coating composition comprising an effective amount of at least one therapeutic agent and/or sunscreen agent for the prevention or treatment of a disorder of the skin wherein, upon application to skin, said coating composition forms the waterproof flexible film.

20. The method of claim 19, wherein said disorder of the skin is xeroderma pigmentosum.

21. A coating composition suitable for use on skin, said composition comprising:
about 1 to 30% w/w resin;
about 40 to 90% w/w alcohol;
about 2 to 58.4% w/w oil;
about 0.5 to 10% w/w cellulosic preparation; and
about 0.1 to 10% w/w inorganic thickener,
wherein the ratio of resin to oil to cellulosic preparation ranges from 0.1:0.2:1 to 60:116.8:1, and wherein the resin is shellac, the alcohol is ethanol, the oil is castor oil or a mixture of castor oil and rosehip oil, the cellulosic preparation is ethyl cellulose, and the inorganic thickener is fumed silica.

22. The coating composition of claim 21, wherein the coating composition further comprises at least one pigment and/or dye.

23. The coating composition of claim 22, wherein the coating composition comprises about 0.01 to 10% w/w pigment and/or dye.

24. The coating composition of claim 22, wherein the coating composition is in a diluted form suitable for application as a spray, and comprises:
about 1.2% w/w shellac;
about 86% w/w ethanol;
about 8% w/w castor oil;
about 2% w/w ethyl cellulose;
about 0.6% w/w fumed silica; and
about 2.2% pigment and/or dye,
wherein the ratio of resin to oil to cellulosic preparation is about 0.7:4.4:1.

25. The coating composition of claim 21, wherein the coating composition further comprises at least one sunscreen agent.

26. The coating composition of claim 25, wherein the coating composition comprises about 10 to 60% w/w sunscreen agent.

27. The coating composition of claim 26, wherein the sunscreen agent comprises zinc oxide.

28. The coating composition of claim 25, wherein the resin is shellac, the alcohol is ethanol, the oil is a mixture of 7 to 15% w/w castor oil and 0.1 to 5% w/w rosehip oil, the cellulosic preparation is ethyl cellulose, and the sunscreen agent is zinc oxide having a particle size of between about 5 to 100 nm.

29. The coating composition of claim 21, wherein the coating composition further comprises at least one therapeutic agent.

30. The coating composition of claim 29, wherein the therapeutic agent comprises about 0.5 to 5% w/w vitamin E acetate.

31. A method of preparing a waterproof flexible colored film for coating a skin discoloration or skin blemish comprising using a coating composition according to claim 22 in the formation of a waterproof flexible colored film, wherein said coating composition comprising an effective amount of at least one pigment and/or dye, such that, upon application to the skin, said composition forms a waterproof flexible colored film over the skin discoloration or blemish so that the skin discoloration or blemish blends with the surrounding skin.

32. The method of claim 31, wherein said coating composition further comprises a sunscreen agent and/or a therapeutic agent.

33. The method of claim 31, wherein the skin discoloration or blemish is selected from the group consisting of a birthmark, a mole, a basal cell carcinoma, vitiligo, a scar, a burn, pigmentation, acne, a vein, tattoo, eczema, dermatitis and bruising.

34. The method of claim 31, wherein the coating composition is formulated to enable the use of a fixing powder on the coated skin discoloration or blemish.

35. The method of claim 34, wherein the fixing powder comprises:
about 93.0% w/w talc;
about 4.7% w/w zinc stearate;
about 1.4% w/w silicone oil; and
about 0.9% w/w preservative.

36. The method of claim 31, wherein the coating composition is formulated as a paste.

37. A method of preparing a waterproof flexible film comprising using a coating composition according to claim 25 in the preparation of the waterproof flexible film, wherein said coating composition comprising an effective amount of at least one therapeutic agent and/or sunscreen agent for the prevention or treatment of a disorder of the skin, and wherein, upon application to skin, said coating composition forms the waterproof flexible film.

38. The method of claim 37, wherein said disorder of the skin is xeroderma pigmentosum.

* * * * *